(12) United States Patent
Yun et al.

(10) Patent No.: US 10,505,201 B2
(45) Date of Patent: Dec. 10, 2019

(54) CNT SHEET SUBSTRATES AND TRANSITION METALS DEPOSITED ON SAME

(71) Applicant: North Carolina Agricultural and Technical State University, Greensboro, NC (US)

(72) Inventors: Yeoheung Yun, Greensboro, NC (US); Youngmi Koo, Greensboro, NC (US); Jagannathan Sankar, Greensboro, NC (US)

(73) Assignee: North Carolina Agricultural and Technical State University, Greensboro, NC (US)

( * ) Notice: Subject to any disclaimer, the term of this patent is extended or adjusted under 35 U.S.C. 154(b) by 357 days.

(21) Appl. No.: 15/116,708

(22) PCT Filed: Feb. 5, 2015

(86) PCT No.: PCT/US2015/014621
§ 371 (c)(1),
(2) Date: Aug. 4, 2016

(87) PCT Pub. No.: WO2015/167637
PCT Pub. Date: Nov. 5, 2015

(65) Prior Publication Data
US 2016/0351918 A1    Dec. 1, 2016

Related U.S. Application Data

(60) Provisional application No. 61/936,129, filed on Feb. 5, 2014, provisional application No. 62/020,690, filed on Jul. 3, 2014.

(51) Int. Cl.
*C23C 16/00* (2006.01)
*B01J 23/40* (2006.01)
(Continued)

(52) U.S. Cl.
CPC .......... *H01M 4/9083* (2013.01); *B01J 27/20* (2013.01); *B01J 35/004* (2013.01); *B32B 37/14* (2013.01);
(Continued)

(58) Field of Classification Search
CPC . B01J 21/185; B01J 23/40; B01J 23/48; B01J 23/72; B01J 23/8926; B01J 35/0033;
(Continued)

(56) References Cited

U.S. PATENT DOCUMENTS 7,041,620 B2 *   5/2006   Smalley .................. B01J 19/081
                                                              502/182
7,538,062 B1 *   5/2009   Dai ........................ B82Y 30/00
                                                              502/185
(Continued)

FOREIGN PATENT DOCUMENTS

WO   WO 2013/016447 A2   1/2013
WO   WO 2015/167637 A2   11/2015

OTHER PUBLICATIONS

Youngmi Koo et al., "Synthesis and characterization of Ag—TiO2-CNT nanoparticle composites with high photocatalytic activity under artificial light." Composites: Part B 57, pp. 105-111. (Year: 2013).*

(Continued)

*Primary Examiner* — Patricia L. Hailey
(74) *Attorney, Agent, or Firm* — Jenkins, Wilson, Taylor & Hunt, P.A.

(57) ABSTRACT

The present subject matter relates generally to the derivatization of highly-aligned carbon nanotube sheet substrates with one or more transition metal centers and to uses of the resulting metal-derivatized CNT sheet substrates.

23 Claims, 24 Drawing Sheets

(51) Int. Cl.
| | |
|---|---|
| B01J 23/48 | (2006.01) |
| B01J 23/72 | (2006.01) |
| H01M 4/90 | (2006.01) |
| B82Y 30/00 | (2011.01) |
| B01J 27/20 | (2006.01) |
| B01J 35/00 | (2006.01) |
| B32B 37/14 | (2006.01) |
| B32B 38/10 | (2006.01) |
| C07C 1/12 | (2006.01) |
| C10G 2/00 | (2006.01) |
| C23C 14/18 | (2006.01) |
| C23C 16/44 | (2006.01) |
| C25B 1/00 | (2006.01) |
| C25B 3/04 | (2006.01) |
| C25D 5/54 | (2006.01) |
| H01M 4/88 | (2006.01) |
| H01M 4/92 | (2006.01) |
| H01M 8/0202 | (2016.01) |
| C01B 32/168 | (2017.01) |
| C01B 32/174 | (2017.01) |
| C01B 32/40 | (2017.01) |

(52) U.S. Cl.
CPC ............. $B32B\ 38/10$ (2013.01); $B82Y\ 30/00$ (2013.01); $C01B\ 32/168$ (2017.08); $C01B\ 32/174$ (2017.08); $C01B\ 32/40$ (2017.08); $C07C\ 1/12$ (2013.01); $C10G\ 2/50$ (2013.01); $C23C\ 14/18$ (2013.01); $C23C\ 16/44$ (2013.01); $C25B\ 1/003$ (2013.01); $C25B\ 3/04$ (2013.01); $C25D\ 5/54$ (2013.01); $H01M\ 4/8817$ (2013.01); $H01M\ 4/8853$ (2013.01); $H01M\ 4/9016$ (2013.01); $H01M\ 4/9041$ (2013.01); $H01M\ 4/921$ (2013.01); $H01M\ 4/923$ (2013.01); $H01M\ 4/926$ (2013.01); $H01M\ 8/0202$ (2013.01); $C07C\ 2521/06$ (2013.01); $C07C\ 2521/18$ (2013.01); $C07C\ 2523/14$ (2013.01); $C07C\ 2523/42$ (2013.01); $C07C\ 2523/50$ (2013.01); $C07C\ 2523/52$ (2013.01); $C07C\ 2523/72$ (2013.01)

(58) Field of Classification Search
CPC ........ B01J 35/004; B05D 3/141; B05D 3/142; B05D 2350/65; C23C 16/00; C23C 16/4414
USPC .......... 502/182, 184, 185; 977/742; 427/123–125, 533, 535, 585
See application file for complete search history.

(56) References Cited

U.S. PATENT DOCUMENTS

| | | | | |
|---|---|---|---|---|
| 2004/0121221 | A1* | 6/2004 | Suzuki | B82Y 30/00 429/532 |
| 2005/0053826 | A1* | 3/2005 | Wang | B82Y 30/00 427/115 |
| 2008/0050640 | A1* | 2/2008 | Sun | H01M 4/8652 502/185 |
| 2010/0140097 | A1* | 6/2010 | Wei | H01M 4/90 205/50 |
| 2010/0160155 | A1* | 6/2010 | Liang | B01J 21/185 502/182 |
| 2010/0177462 | A1* | 7/2010 | Adzic | B82Y 30/00 361/502 |
| 2011/0194990 | A1* | 8/2011 | Hsu | B01J 21/063 422/211 |
| 2012/0100203 | A1 | 4/2012 | Fang et al. | |
| 2012/0247180 | A1 | 10/2012 | Llobet Valero et al. | |
| 2013/0026029 | A1 | 1/2013 | Kayaert et al. | |
| 2013/0048506 | A1 | 2/2013 | Chen et al. | |
| 2013/0062216 | A1 | 3/2013 | Yotsuhashi et al. | |
| 2016/0107149 | A1* | 4/2016 | Gopinath | B01J 27/24 502/5 |

OTHER PUBLICATIONS

D. Banerjee et al., "Synthesis of SnO2 functionalized amorphous carbon nanotube for efficient electrron field emission application." Journal of Alloys and Compounds 572, pp. 49-55. (Year: 2013).*

Yang An et al., "Synthesis and characterization of carbon nanotubes-treated Ag@TiO2 core-shell nanocomposites with highly enhanced photocatalytic performance." Optical Materials 36, pp. 1390-1395. (Year: 2014).*

Arai et al., "Cu-MWCNT composite films fabricated by electrodeposition," J. Electrochemical Society, vol. 157, No. 3, pp. D147-D153 (2010).

Barcena et al., "Novel copper/carbon nanofibres composites for high thermal conductivity electronic packaging,", pp. 1-8, (2006) Downloaded from http:escies.org/download/webDocumentFile?id=1691.

Bittencourt et al., "Metallic nanoparticles on plasma treated carbon nanotubes: nano2hybrids," Surface Science, vol. 601, pp. 2800-2804 (2007).

Bittencourt et al., "Study of the interaction between copper and carbon nanotbues," Chemical Physics Letters, vol. 535, pp. 80-83 (2012).

Chen et al., "Electrocatalytic activity of spots of electrodeposited noble-metal catalysts on carbon nanotubes modified glassy carbon," Anal. Chem., vol. 81, pp. 7597-7603 (2009).

Chen et al., "Improved field emissino performance of carbon nanotube by introducing copper metallic particles," Nanoscale Research Letters, vol. 6, pp. 1-8 (2011).

Chu et al., "Thermal properties of carbon nanotube-copper composites for thermal management applications," Nanoscale Res. Lett., vol. 5, No. 5, pp. 868-874 (2010).

Diasio, "Electrodeposition of metals onto aligned carbon nanotube microstructures," 2011 NNIN REU Research Accomplishements, pp. 190-191 (2011); downloaded from www.nnin.org/sites/default/files/files/2011NNINreuRA/2011NNINreuRA_Diasio.pdf.

Goncalves et al., Selective electrochemical conversion of CO2 to C2 hydrocarbons, Energy Conversion and Management, vol. 51, pp. 30-32 (2010).

Jesús-Cardona et al., "Voltammetric study of CO2 reduction at Cu electrodes under different KHCO3 concentrations, temperatures and CO2 proessures," J. Electroanalytical Chemistry, vol. 513, pp. 45-51 (2001).

Jakubinek et al., "Thermal and electrical conductivity of array-spun multi-walled carbon nanotube yarns," Carbon, vol. 50, No. 1, pp. 244-248 (2012).

Jayalakshmi et al., "Cyclic voltammetric behavior of copper powder immobilized on paraggin impregnated graphite electrode in dilute alkali solution," Int. J. Electrochem. Sci., vol. 3, pp. 1277-1287 (2008).

Jiang and Jiang, "Carbon nanotubes supported metal nanoparticles for the applications in proton exchange membrane fuel cells (PEMFCs)," in Carbon Nanotubes—Growth and Applications, Dr. Mohammad Naraghi (Ed.), InTech, pp. 567-605 (2011); downloaded from http://www/intechopen.com/books/carbon-nanotubes-growth-and-applications/carbon-nantubes-supported-metal-nanoparticles-for-the-applications-in -proton-exchange-membrane-fuel.

Keerthiga et al., "Electrochemical reduction of carbon dioxide at surface oxidized copper electrode," Bonfring International Journal of Industrial Engineering and Management Science, vol. 2, No. 1, pp. 41-43 (2012).

Koo et al., "Aligned carbon nanotube/copper sheets: a new electrocatalyst for CO2 reduction to hydrocarbons," RSC Advances, vol. 4, pp. 16362-16367 (Mar. 13, 2014).

Koo et al., "Free-standing carbon nanotube-titania photoactive sheets," J. Colloid and Interface Sci., vol. 448, pp. 148-155 (Feb. 14, 2015).

(56) References Cited

OTHER PUBLICATIONS

Malik et al., "Manufacturing and applications of carbon nanotube sheet," in Recent Advances in Circuits, Communications and Signal Processing, Proceedings of the 5th International Conference on Nanotechnology, WSEAS Press, pp. 327-335 (Feb. 2013).
Notification of Transmittal of the International Search Report and Written Opinion of the International Searching Authority, or Decaration, corresponding to International Patent Application Serial No. PCT/US2015/014621 dated Dec. 14, 2015.
Notification Concerning Transmittal of International Preliminary Report on Patentability (Chapter I of the Patent Cooperation Treaty), corresponding to International Patent Application Serial No. PCT/US2015/014621 dated Aug. 18, 2016.
O'Byrne et al., "High CO2 and CO conversion to hydrocarbons using bridged Fe nanoparticles on carbon nanotubes," Catalysis Science and Technology, vol. 3, No. 5, pp. 1202-1207 (Feb. 6, 2013).
Oliveria et al., "Evaluation of carbon nanotube paste electrode modified with copper microparticles and its application to determinatino of quercetin," Int. J. Electrochem. Sci., vol. 6, pp. 804-818 (2011).
Oztekin et al., "Copper nanoparticle modified carbon electrode for determination of dopamine," Electrochimica Acta, vol. 76, pp. 201-207 (2012).
Pöhls, et al., "Physical properties of carbon nanotube sheets drawn from nanotube arrays," Carbon, vol. 50, No. 11, pp. 4175-4183 (2012).
Rosen et al., "Ionic liquid-mediated selective conversion of CO2 to CO at low overpotentials," Science, vol. 334, No. 6056, pp. 643-644 (2011).
Schouten et al., "Structure sensitivity of the electrochemical reduction of carbon monoxide on copper single crystals," ACS Catal., vol. 3, pp. 1292-1295 (May 8, 2013).
Srivastava et al., "Carbon nanotube filters," Nature Materials, vol. 3, No. 9, pp. 610-614 (2004).
Takahashi et al., "Electrochemical reduction of CO2 at copper single crystal CU(S)-[n(111)×(111)] and Cu(s)-[n(110)×(100)] electrodes," J. Electroanalytical Chemistry, vol. 533, pp. 135-143 (2002).
Thorson et al., "Effect of cations on the electrochemical conversion of CO2 to CO," J. Electrochemical Society, vol. 160, No. , pp. F69-F74 (2013; published Nov. 9, 2012).
Whipple et al., "Microfluidic reactor for the electrochemical reduction of carbon dioxide: the effect of pH," Electrochemical and Solid-State Letters, vol. 13, No. 9, pp. B109-B111 (2010).
Wu et al., "Electrochemical reduction of carbon dioxide I. Effects of the electrolyte on the selectivity and activity with Sn electrode," J. Electrochemical Society, vol. 159, No. 7, pp. F353-F359 (2012).
Wu et al., "Electrochemical reduction of carbon dioxide II. Design, assembly, and performance of low temperature full electrochemical cells," J. Electrochemical Society, vol. 160, No. 9, pp. F953-F957 (Jun. 18, 2013).
Yan et al., "Preparation and electrochemical properties of composites of carbon nanotubes loaded with Ag and TiO2 nanoparticle for use as anode material in lithium-ion batteries," Electrochemica Acta, vol. 53, pp. 6351-6355 (2008).
Zhao, "Super-long aligned TiO2/carbon nanotbue arrays," Nanotechnology, vol. 21, pp. 1-7 (2010).
Zhou et al., "Preparation of crystalline Sn-doped TiO2 and its application in visible-light photocatalysis," Journal of Nanomaterials, vol. 47 (2011).
Chang et al., "Flexible direct-growth CNT biosensors," Biosensors and Bioelectronics, vol. 41, pp. 898-902 (2013).
Dillon, "Carbon nanotubes for photoconversion and electrical energy storage," Chem. Rev., vol. 110, No. 11, pp. 6856-6872 (2010).
Felten et al., "Effect of oxygen rf-plasma on electronic properties of CNTs," J. Phys. D: Appl. Phys., vol. 40, pp. 7379-7382 (2007).
Gattrell et al., "A review of the aqueous electrochemical reduction of CO2 to hydrocarbons at copper," J. Electroanalytical Chemistry, vol. 594, pp. 1-19 (2006).
Hori et al., "Production of CO and CH4 in electrochemical reduction of CO2 at metal electrodes in aqueous hydrogencarbonate solution," Chemistry Letters, vol. 14, No. 11, pp. 1695-1698 (1985).
Hrapovic et al., "Metallic nanoparticle-carbon nanotube composites for electrochemical determination of explosive nitroaromatic compounds," Anal. Chem., vol. 78, pp. 5504-5512 (2006).
Kang et al. "A sensitive nonenzymatic glucose sensor in alkaline media with a copper nanocluster/multiwall carbon nanotube-modified glassy carbon electrode," Analytical Biochemistry, vol. 363, pp. 143-150 (2007).
Kim et al., "Synthesis and Electrochemical Properties of Spin-Capable Carbon Nanotube Sheet/MnOx Composites for High-Performance Energy Storage Devices," Nano Lett., vol. 11, pp. 2611-2617 (2011).
Ko et al., "Photochemical synthesis and photocatalytic activity in simulated solar light of nanosized Ag doped TiO2 nanoparticle composite," Composites Part B, vol. 42, No. 3, pp. 579-583 (2011).
Koo et al., "Inverse-ordered fabrication of free-standing CNT sheets for supercapacitor," Langmuir, vol. 31, No. 27, pp. 7616-7622 (Jun. 17, 2015).
Liang, et al. "TiO2 nanocrystals grown on graphene as advanced photocatalytic hybrid materials," Nano Res., vol. 3, No. 10, pp. 701-705 (2010).
Valentini et al., "The electrochemical detection of ammonia in drinking water based on multi-walled carbon nanotube/copper nanoparticles composite paste electrodes," Sensors and Actuators B, vol. 128, pp. 326-333 (2007).
Wang et al., "Preparation and photocatalytic properties of silver nanoparticles loaded on CNTs/TiO 2 composite," Applied Surface Science, vol. 255, No. 18, pp. 8063-8066 (2009).
Woan et al., "Photocatalytic carbon-nanotube-TiO2 composites," Adv. Mater., vol. 21, pp. 2233-2239 (2009).
Xia et al., "Preparation of multi-walled carbon nanotube supported TiO2 and its photocatalytic activity in the reduction of CO2 with H2O." Carbon, vol. 45, pp. 717-721 (2007).
Xu et al., "Continuous electrodeposition for lightweight, highly conducting and strong carbon nanotube-copper composite fibers," Nanoscale, vol. 3, pp. 4215-4219 (2011).
Zhang et al., "Strong, transparent, multifunctional, carbon nanotube sheets," Science, vol. 19, No. 5738, pp. 1215-1219 (2005).
Zhang et al., "Photoelectrocatalytic properties of Ag-CNT/TiO2 composite electrodes for methylene blue degradation," New Carbon Materials, vol. 25, No. 5, pp. 348-356 (Jun. 2010).

* cited by examiner

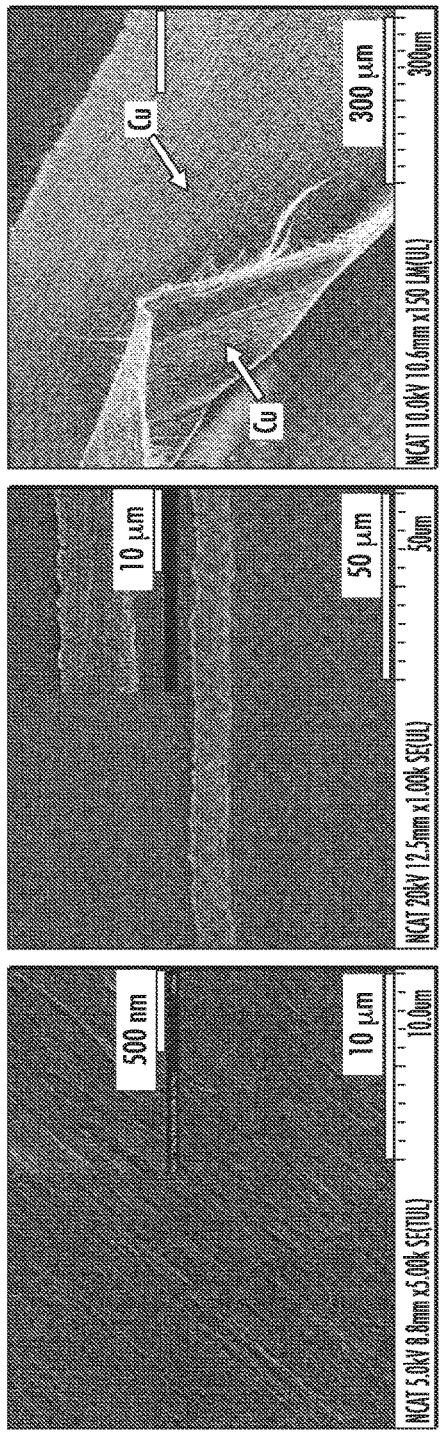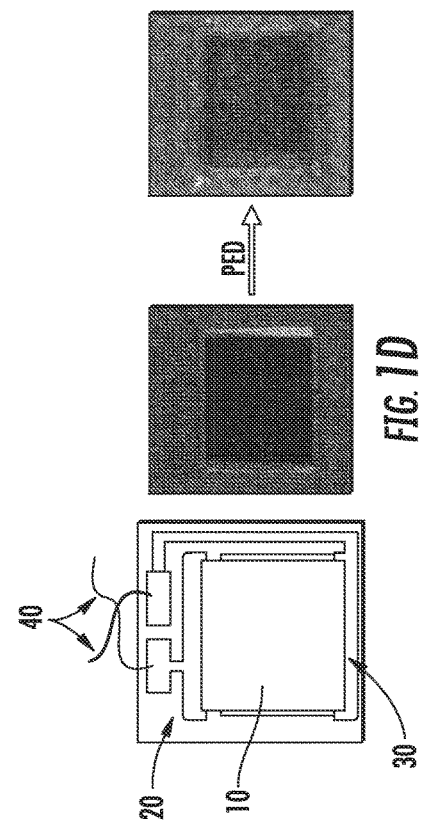
FIG. 1A  FIG. 1B  FIG. 1C  FIG. 1D (C)

CNT SHEET SUBSTRATES AND TRANSITION METALS DEPOSITED ON SAME

CROSS-REFERENCE TO RELATED APPLICATIONS

This application claims priority under 35 U.S.C. § 119(e) to U.S. Provisional Patent Application Ser. No. 61/936,129 filed Feb. 5, 2014 and 62/020,690, filed Jul. 3, 2014, the disclosure of each of which is incorporated herein by reference in its entirety.

STATEMENT AS TO RIGHTS TO INVENTIONS MADE UNDER FEDERALLY SPONSORED RESEARCH OR DEVELOPMENT

Work described herein was supported by the Office of Naval Research (N0001411103151) The United States Government therefore has certain rights in the inventions.

FIELD

The presently disclosed subject matter relates generally to the preparation of substrates comprising carbon nanotube sheets and to derivatization of highly-aligned carbon nanotube sheets with one or more transition metal centers.

BACKGROUND

Since the discovery of carbon nanotubes (CNTs) in 1991, CNTs have been used in various fields including energy storage, molecular electronics, nanoprobes, sensor, and composite materials. The excellent mechanical, electrical, and thermal properties of CNTs have also led to the emergence of CNTs as electrocatalysts, either as a stand-alone electrode with the necessary binder or as additionally modified with metal centers with added binders. CNT sheets have been prepared that are flexible, stackable with multi-layers, reusable, much lighter than metal, and are conductive.

However, CNTs are still challenged with the controllability in alignment-dependent, interconnection-dependent, and layered thickness-dependent electrical conductivity. Although it has been shown that chemical vapor deposition (CVD) can be used to fabricate CNT arrays (see for example, Jakubinek, M. B., Johnson, M. B., White, M. A., Jayasinghe, C., Li, G., Cho, W., Schulz, M. J., and Shanov. "Thermal and electrical conductivity of array-spun multi-walled carbon nanotube yarns." Carbon 50, no. 1 (2012): 244-248), it is challenging to fabricate low resistance and thin layer CNT sheets. Specific challenges include: 1) handling CNT sheets, in particular for cutting, bonding, and electrically connecting the sheets, and 2) transporting CNT sheets from one place to other without damaging them.

SUMMARY

The present application is generally directed to methods for the preparation of CNT sheets substrates as well as the deposition of metal centers on CNT sheets or CNT substrates and the products resulting therefrom.

In one aspect, the present application discloses a method of preparing a CNT sheet substrate comprising between about 5 and about 100 CNT sheets. In one variation, the 5-100 CNT sheet substrate is prepared from a CNT sheet substrate comprising at least about 200 CNT sheets.

In a further aspect, the present application discloses a CNT sheet or CNT substrate derivatized with one or more metal centers selected from the group of Cu, Pt, Ru, Ti, Pd, Sn, Ag, Au, CuO, $Cu_2O$, $TiO_2$, PdO, SnO, AgO, AuO, Ag/Ti, Pt/Ru, $Ag/TiO_2$, $Sn/TiO_2$, $Pt/TiO_2$, $Au/TiO_2$, and $Pt/Al_2O_3$. In another aspect, the present application discloses a catalyst comprising a metal-derivatized CNT sheet substrate. In yet another aspect, the present application discloses a method of converting carbon dioxide to one or more or carbon monoxide, methane, ethane, higher order hydrocarbons or a combination comprising exposing carbon dioxide to a catalyst comprising a metal-derivatized CNT sheet substrate. Alternately, the present application discloses each of a method of filtering biological contaminants from a biological sample and a method of filtering volatile organic compounds from a non-biological sample comprising passing the biological sample or non-biological sample comprising biological or VOC contaminants respectively through or past a metal-derivatized CNT sheet or a metal-derivatized CNT substrate as disclosed herein and separating the unwanted contaminants from the sample. In yet another aspect, the present application discloses each of an energy storage device, a fuel cell electrode, and a biosensor each of which comprise a metal-derivatized CNT sheet or CNT substrate as disclosed herein.

In another aspect, the present application discloses a method of preparing a CNT sheet or CNT substrate derivatized with one or more transition metal centers comprising: (a) treating a CNT sheet or CNT substrate with oxygen plasma yielding a functionalized CNT sheet or functionalized CNT substrate; and (b) depositing one or more transition metals on the functionalized CNT sheet or functionalized CNT substrate.

In another aspect, the present application discloses electrochemically depositing one or more metal centers on CNT sheets or CNT substrates as disclosed herein, without a prior treatment step, such as oxygen plasma.

In another aspect, the present application discloses a method for fabricating of a CNT sheet substrate, the method comprising: (a) providing a first CNT sheet substrate having a first thickness defined by a number of CNT sheets; (b) providing a template sheet having an aperture therein, the aperture having a predetermined dimension; (c) adhering the template sheet to the first CNT sheet substrate; and (d) pulling the template sheet away from the first CNT sheet substrate to form a second CNT sheet substrate of a second thickness and having the predetermined dimension of the aperture, wherein the second thickness is not as great as the first thickness.

Accordingly, it is an object of the presently disclosed subject matter to provide methods for the preparation of CNT sheets and CNT substrates, as well as the deposition of metal centers on CNT sheet and CNT substrates and products resulting therefrom. This object is achieved in whole or in part by the presently disclosed subject matter will become apparent to those skilled in the art after a reading of the following description of the disclosure when considered with the drawings.

BRIEF DESCRIPTION OF THE DRAWINGS

It will be understood that the drawings are for the purpose of describing a preferred embodiment of the inventions and are not intended to limit the inventions thereto.

FIGS. 1A-1C provides a series of images of one alternative fabrication of a derivatized CNT sheet electrode containing Cu centers as disclosed herein.

FIG. 1A is a scanning electron microscopy (SEM) image of a flexible CNT sheet substrate;

FIG. 1B is an SEM cross-section of Cu pulsed-electrode-posited on a substrate having 200 CNT sheets;

FIG. 1C is an image of a Cu-derivatized CNT sheet electrode containing metal centers affixed to both sides of the CNT sheet electrode; and FIG. 1D is a cartoon of a Cu-CNT sheet electrode and a schematic for manufacture of a Cu-CNT sheet electrode.

FIG. 2A is a SEM image of Cu pulse-electrodeposited directly on a CNT sheet substrate (Cu CNT).

FIG. 2B is a SEM image of Cu pulse-electrodeposited on a CNT sheet substrate after $O_2$ plasma pretreatment (Cu—O-CNT).

FIG. 2C is a SEM image of Cu pulse-electrodeposited on a CNT sheet substrate that was activated by cyclic voltammetry after $O_2$ plasma pretreatment (Cu-OE-CNT).

FIGS. 2D-2F are SEM images of side views of the metal centers of each of Cu-CNT, Cu—O-CNT, and Cu-OE-CNT sheet substrates.

FIG. 4A, in an $N_2$-saturated aqueous solution; and

FIG. 4B, in a $CO_2$-saturated aqueous solution.

FIG. 7A is a graph of the current density during electrochemical deposition of CNT-$TiO_2$-1 (deposition time t=3 min), CNT-$TiO_2$-2 (deposition time t=10 min), CNT-$TiO_2$-3 (deposition time t=30 min), and CNT-$TiO_2$-4 (deposition time t=60 min).

FIG. 7B an SEM image of $TiO_2$ nanoparticles affixed to the top and bottom of the CNT sheet substrate (CNT-$TiO_2$-1).

FIG. 7C is a set of SEM images of (a) CNT-$TiO_2$-1 substrate, (b) CNT-$TiO_2$-2 substrate, (c) CNT-$TiO_2$-3 substrate, and (d) CNT-$TiO_2$-4 substrate. Insets are cross-section images of electrochemically deposited $TiO_2$ on CNT sheet substrates.

FIG. 9A presents a series of Nyquist plots of CNT sheet substrate (closed squares) and the four different CNT-$TiO_2$ sheet substrates (CNT-$TiO_2$-1, closed circles; CNT-$TiO_2$-2, closed triangles; CNT-$TiO_2$-3, closed inverted triangles; CNT-$TiO_2$-4, closed diamonds) under UV light off.

FIG. 9B presents a series of Nyquist plots of CNT sheet substrate (closed squares) and the four different CNT-$TiO_2$ (CNT-$TiO_2$-1, closed circles; CNT-$TiO_2$-2, closed triangles; CNT-$TiO_2$-3, closed inverted triangles; CNT-$TiO_2$-4, closed diamonds) sheets under UV illumination.

The Nyquist plots show the imaginary part (Y axis) versus the real part (X axis) of impedance. The inset using the same symbols shows an expanded view of the high frequency range. Data were collected in the frequency range of 1.0 MHz to 0.1 Hz at AC amplitude of 10 rms mV in 0.1 M KCl electrolyte, 2.68 $mW/cm^2$ light intensity, the solutions had been purged with inert gas (either argon or nitrogen).

Figure 10A:
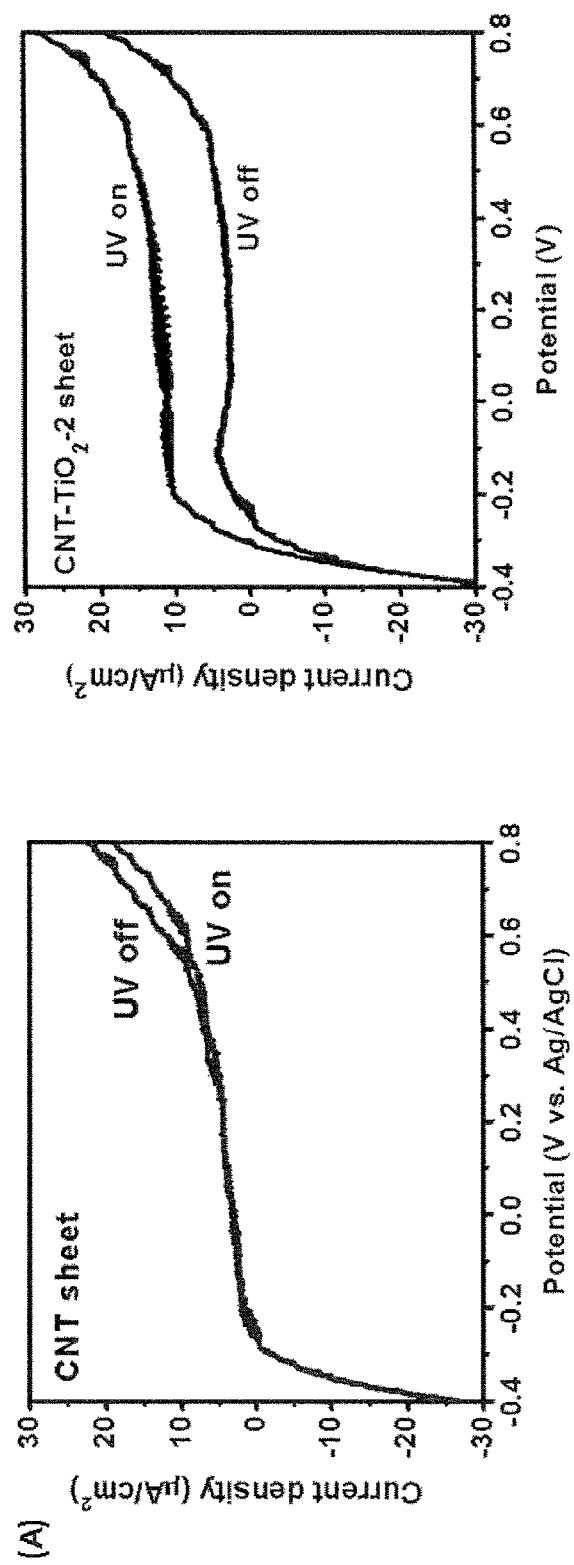
Figure 10B:
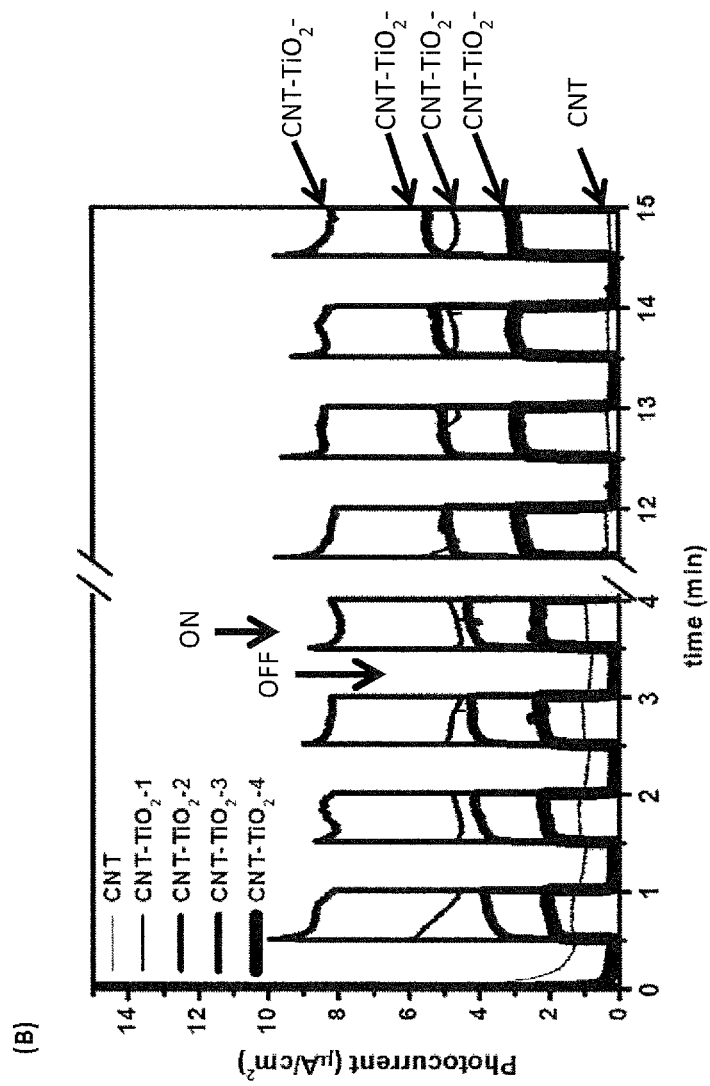

FIGS. 10A and 10B show the photoactive responses of a number of samples prepared according to the methods disclosed herein:

FIG. 10A, photocurrent density vs applied potential (J-V) curves of CNT sheet substrate and CNT-$TiO_2$-2 substrate.

FIG. 10B, transient photocurrent response at a bias voltage of 0.2 V (vs SCE) of the CNT sheet substrate and four different CNT-$TiO_2$ sheet substrates.

The light intensity was 2.68 $mW/cm^2$ and the solution was 0.1M KCl electrolyte purged with $N_2$.

Figures 11A, 11B:
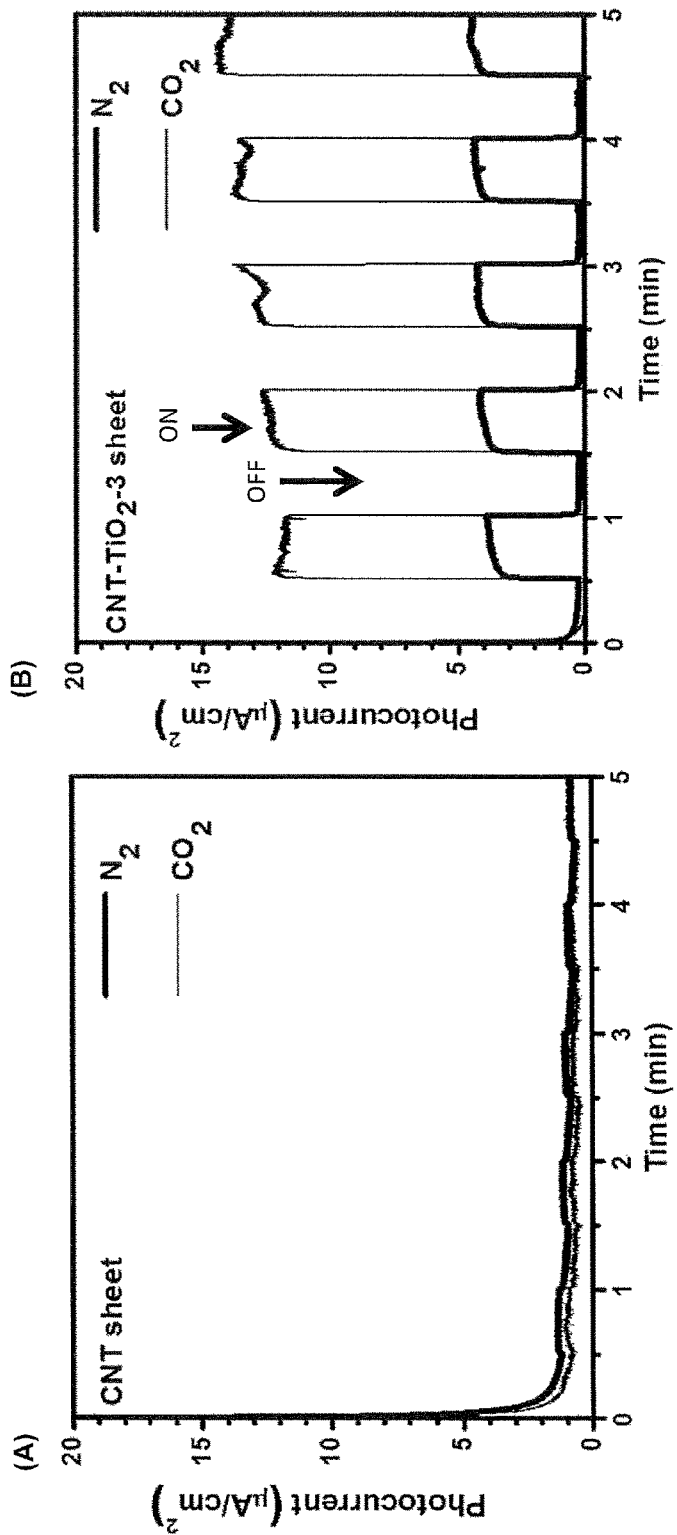

FIGS. 11A and 11B are plots showing a comparison with photocurrent responses:

FIG. 11A, transient photocurrent response of CNT sheet substrate under a UV light switched on/off under $N_2$ and $CO_2$ atmospheres.

FIG. 11B, photocurrent of CNT-$TiO_2$-3 sheet substrates under a UV light switched on/off under $N_2$ and $CO_2$ atmospheres.

Each response was measured with a UV lamp intensity of 2.68 $mW/cm^2$ in 0.1M KCl electrolyte purged with $N_2$ or $CO_2$.

Figure 12:
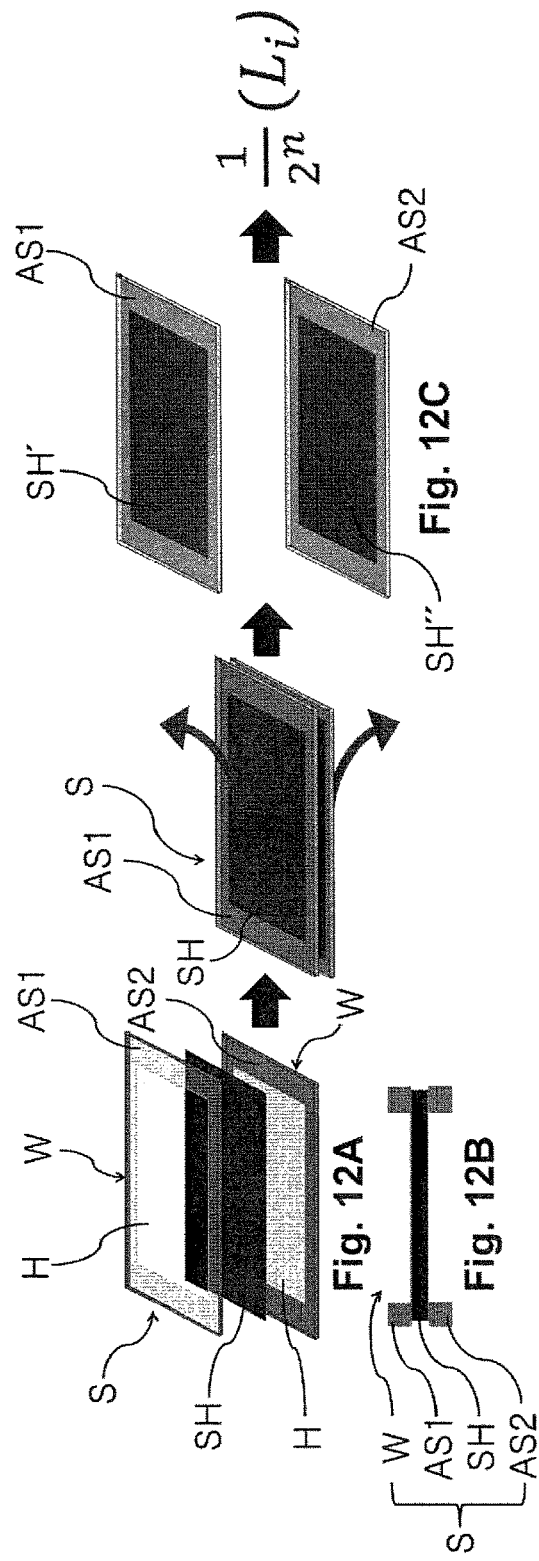

FIG. 12 is a schematic illustration of a method disclosed herein for the preparation of CNT sheet substrates.

Figure 13:
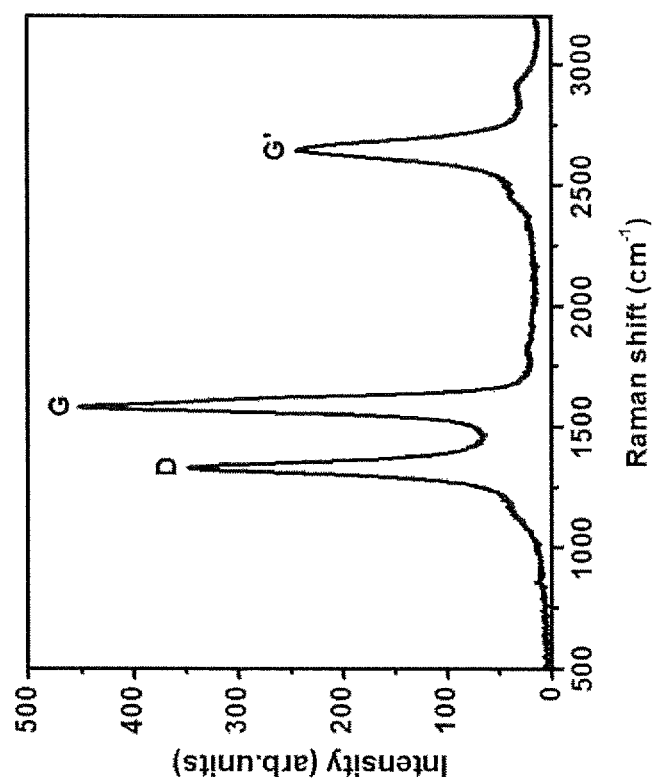

FIG. 13 is a Raman spectrum of a 200 CNT sheet substrate.

Figures 14A, 14B:
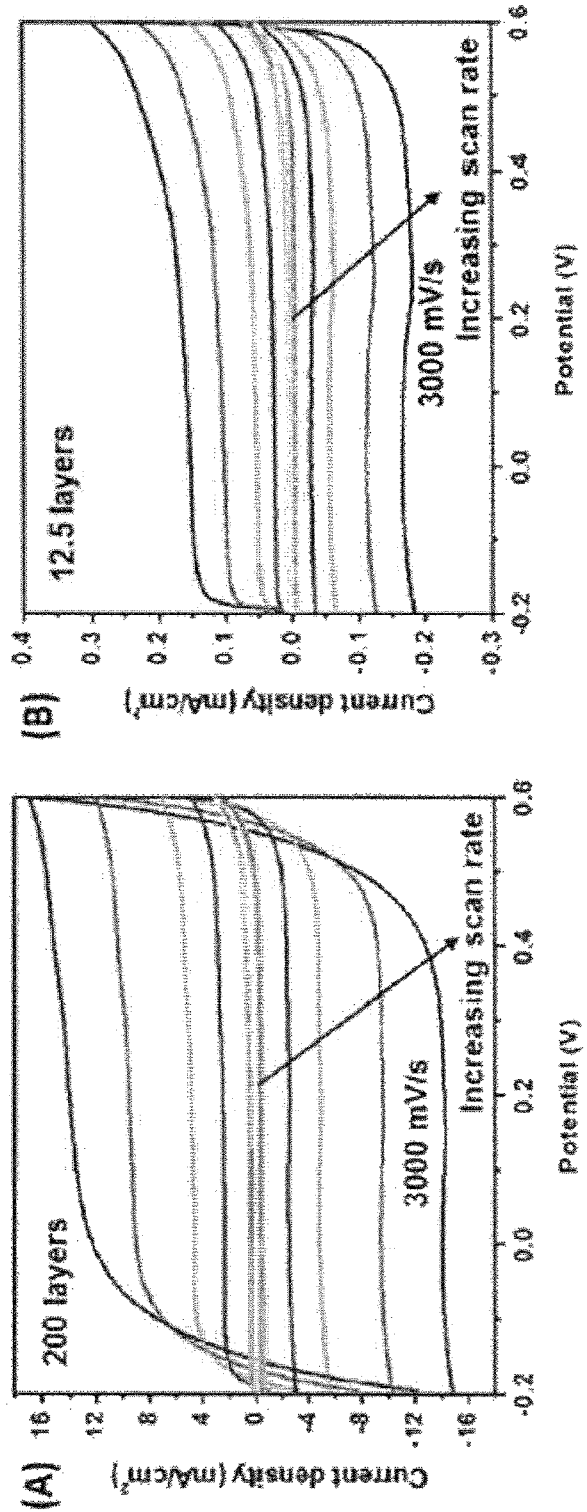
Figures 14C, 14D:
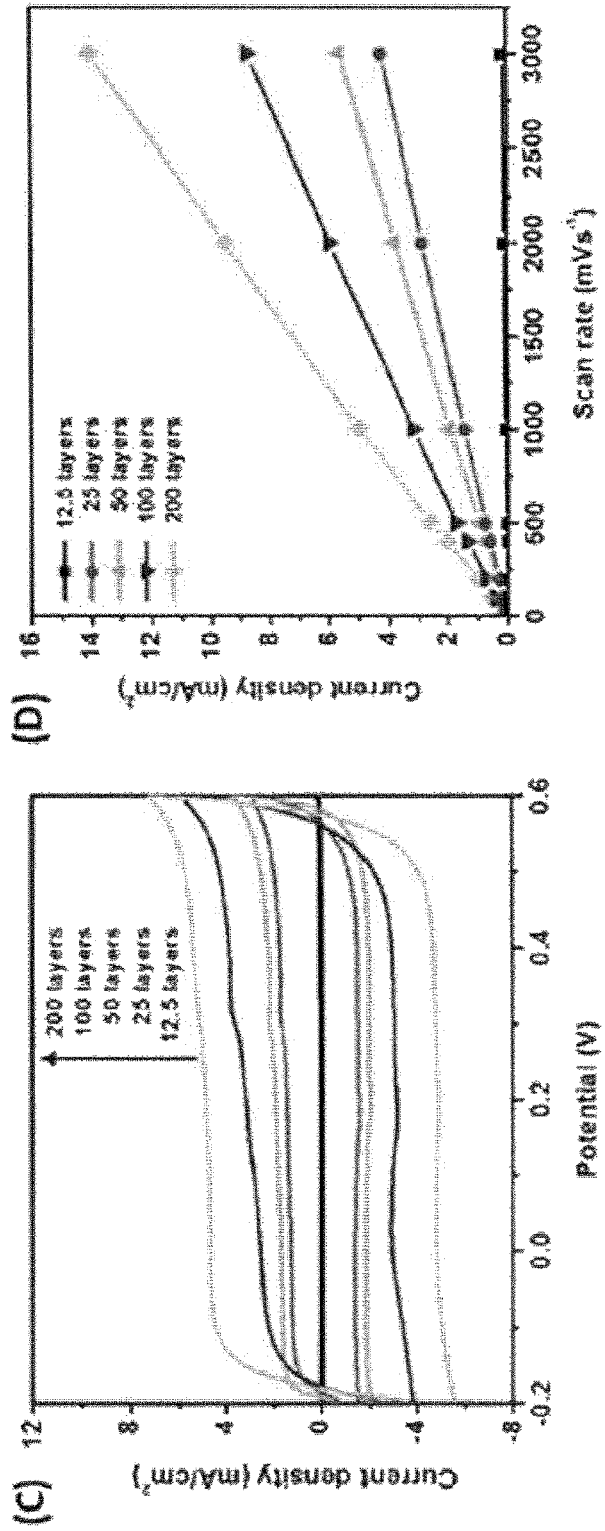

FIGS. 14A-14D are cyclic voltammograms (CVs) obtained in 6 M KOH for an electrode made from CNT substrates of varying number of CNT sheets:

FIG. 14A, 200 CNT sheets;

FIG. 14B, about 12.5 CNT sheets;

FIG. 14C, CVs of various CNT sheet substrates (about 12.5 layers, about 25 layers, about 50 layers, about 100 layers, and about 200 layers), at constant scan rate, 1000 mV/s;

FIG. 14D, comparison of current densities of various CNT sheet substrates at scan rates of 25 mV/s, 50 mV/s, 100 mV/s, 500 mV/s, 1000 mV/s, 2000 mV/s, 3000 mV/s at 0.2 V potential: about 12.5 layers, solid squares; about 25 layers, solid circles; about 50 layers, solid triangles; about 100 layers, solid inverted triangles; about 200 layers, solid diamonds.

Figure 15A:
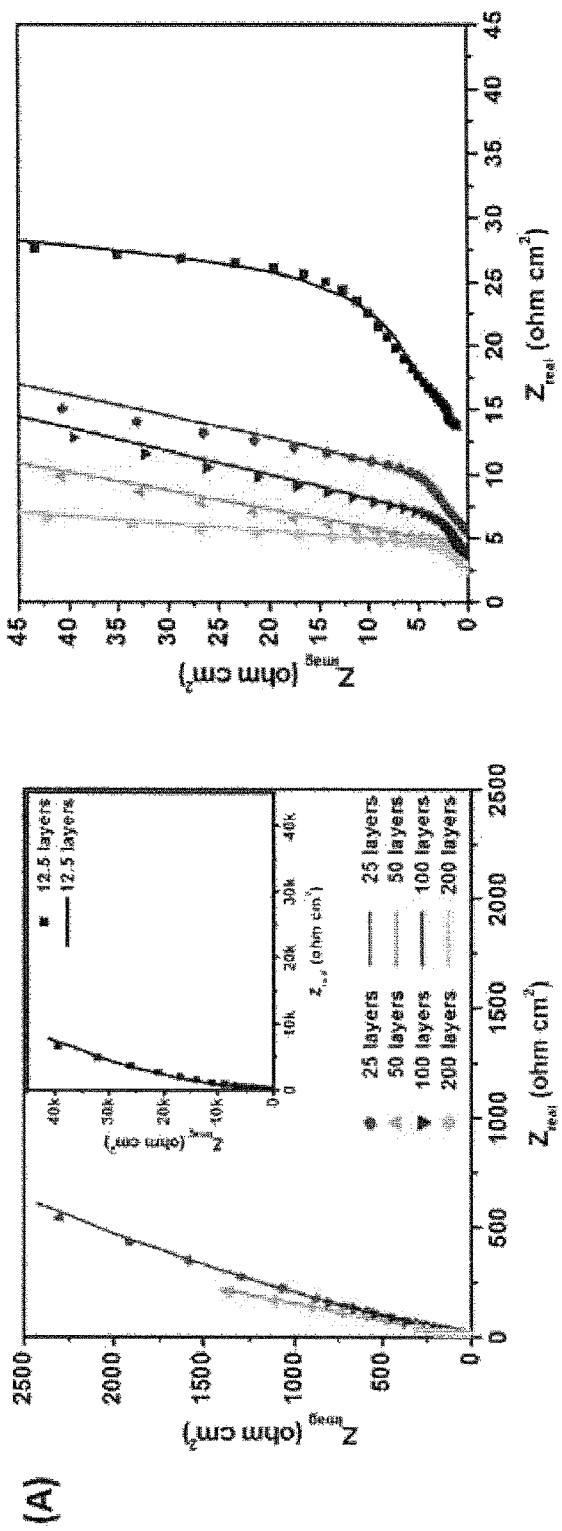
Figure 15B:
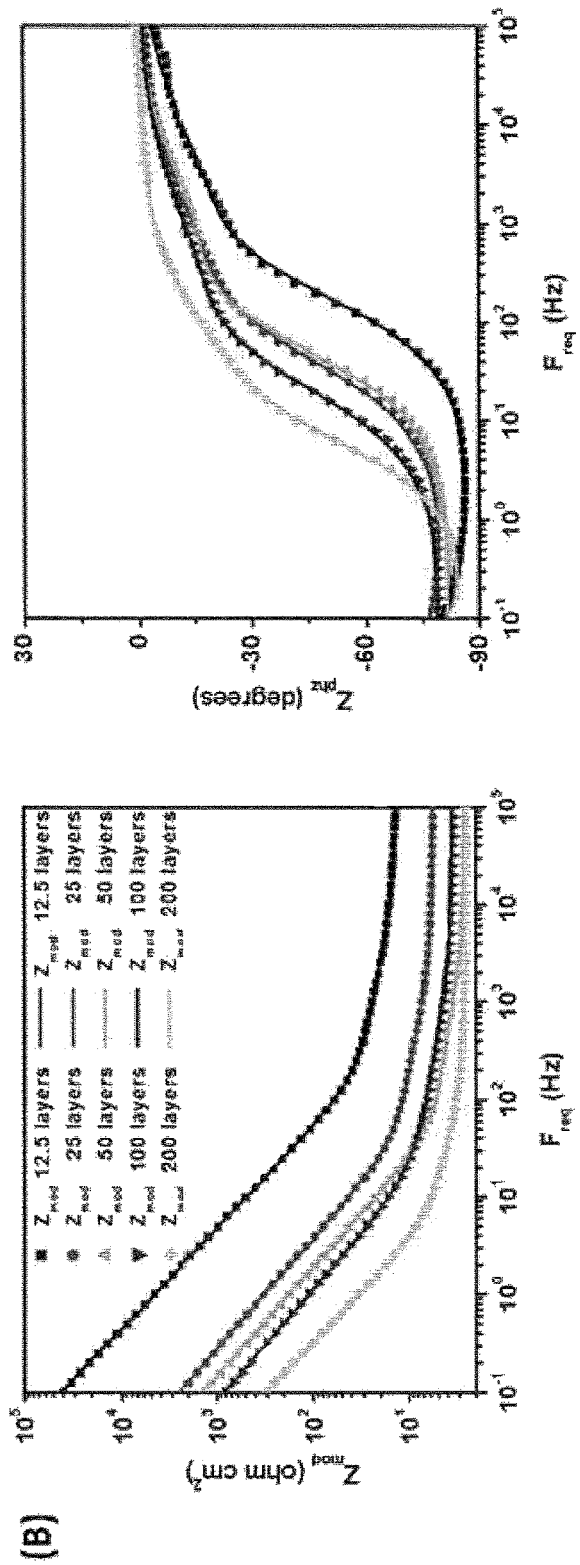
Figure 15C:
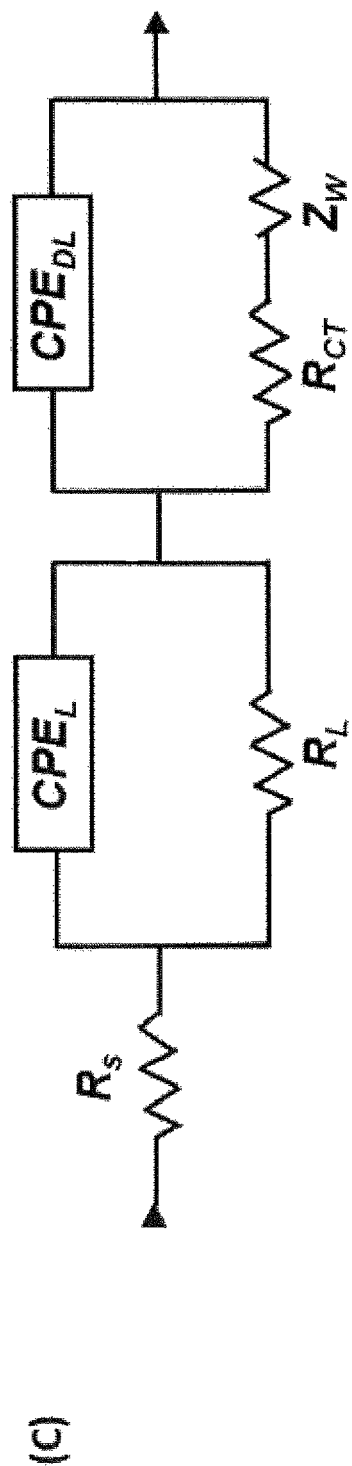

FIGS. 15A-15C are impedance plots for electrodes comprising CNT sheet substrates (which do not require additional binder or physical support) in 6 M KOH:

FIG. 15A is a Nyquist diagram of substrates comprising about 200 CNT sheets (solid diamonds), about 100 CNT sheets (solid inverted triangles), about 50 CNT sheets (solid triangles), about 25 CNT sheets (solid circles), and about 12.5 CNT sheets (solid squares) with frequency ranging from 100 kHz to 0.1 Hz;

FIG. 15B are Bode plots of substrates comprising about 200 CNT sheets (solid diamonds), about 100 CNT sheets (solid inverted triangles), about 50 CNT sheets (solid triangles), about 25 CNT sheets (solid circles), and about 12.5 CNT sheets (solid squares) between 100 kHz and 0.1 Hz frequency; and FIG. 15C, an equivalent circuit for the impedance spectra of substrates comprising different numbers of CNT sheets.

Figure 16A:
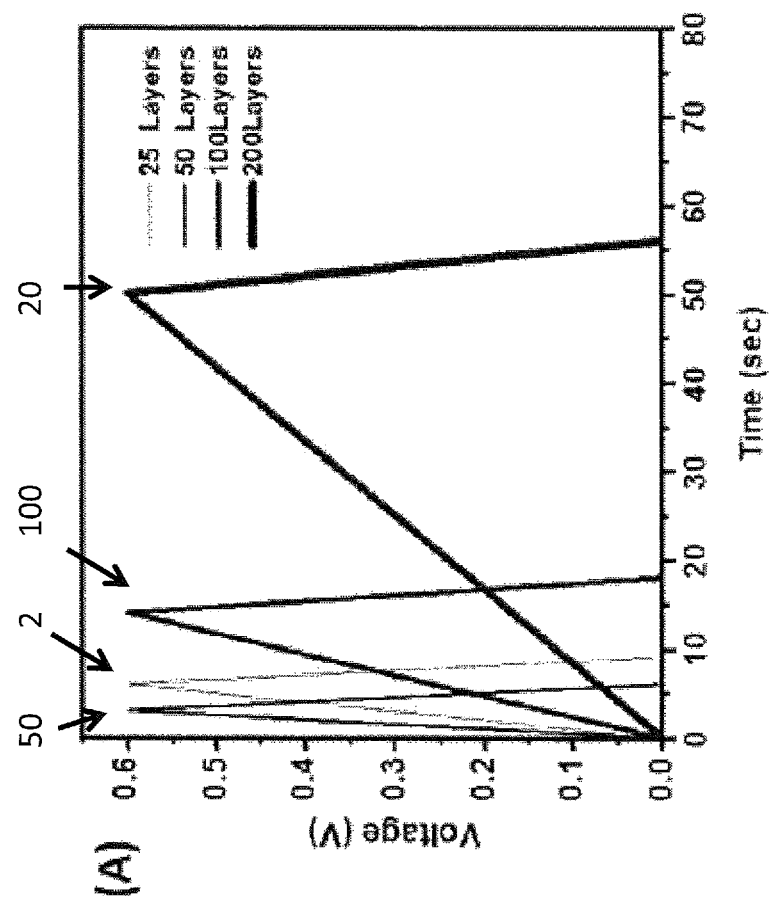
Figure 16B:
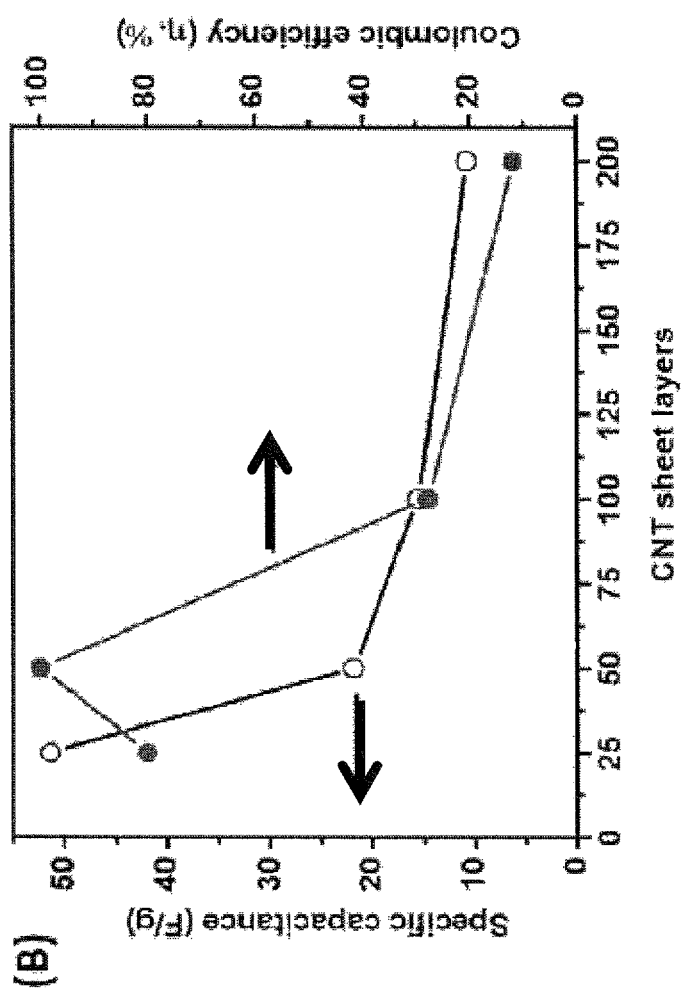
Figure 16C:
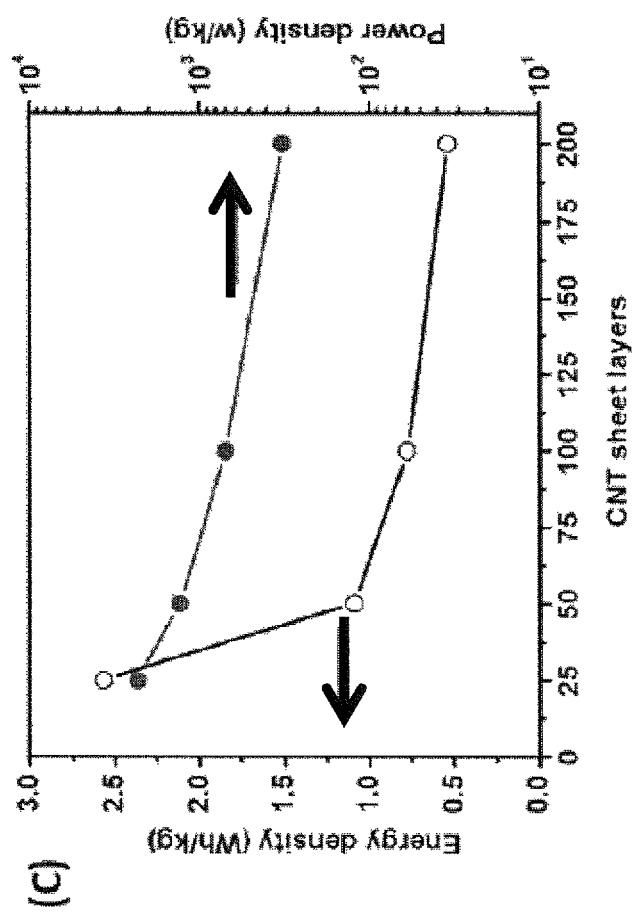

FIGS. 16A-16C are plots showing the electrochemical behavior of electrodes comprising CNT sheets as supercapacitors:

FIG. 16A, galvanostatic charge/discharge curves at 1.5 mA for substrates comprising about 200, about 100, about 50 and about 25 CNT sheets;

FIG. 16B, specific capacitance of CNT substrates comprising about 200, about 100, about 50, about 25, and about 12.5 CNT sheets; Coulombic efficiency as a function of substrates comprising about 200, about 100, about 50, about 25, and about 12.5 CNT sheets, and FIG. 16C, energy and power density of the supercapacitor (in the 6 M KOH electrolyte) as a function of the number of CNT sheets.

DETAILED DESCRIPTION

In accordance with the present application and as used herein, the following terms are defined with the following meanings, unless explicitly stated otherwise.

As used herein, "CNT sheet" refers to a roughly 3-dimensional arrangement of highly aligned multiwalled carbon nanotubes. Methods of preparation of CNT sheets have been reported, including but not limited to: (a) Pöhls, J. H., Johnson, M. B., White, M. A., Malik, R., Ruff, B., Jayasinghe, C., Schulz, M. & Shanov, V. (2012). "Physical properties of carbon nanotube sheets drawn from nanotube arrays." Carbon, 50(11), 4175-4183; (b) Malik, R et al., "Manufacturing and Applications of Carbon Nanotube Sheet" Recent Advances in Circuits, Communications and Signal Processing, from the February 2013 Proceedings of the 5$^{th}$ International Conference on Nanotechnology, (c) Koo, Y.; Malik, R.; Alvarez, N.; White, L.; Shanov, V. N.; Schulz, M.; Collins, B.; Sankar, J.; Yun, Y. *RSC Advances* 2014, 4, 16362-16367, each of which is incorporated in its entirety. Other examples of CNT sheet preparations can be found in Zhang, et al., "Strong, Transparent, Multifunctional, Carbon Nanotube Sheets" *Science* 19, 1215-1219 (2005).

As used herein, "substrate" or "CNT sheet substrate" or "CNT substrate" refers to multiple layers of CNT sheets, wherein the layers are held together either physically or chemically, generally via Van der Waals forces. As used herein, "substrate" or "CNT sheet substrate" or "CNT substrate" does not refer to a nanocomposite and nor does it refer to a composition containing polymer components.

Typically, the substrate contains at least two CNT sheets. In one variation, the CNT sheet substrate contains at least about 5 CNT sheets, at least about 10 CNT sheets, at least about 25 CNT sheets, at least about 50 CNT sheets; in another variation at least about 100, or at least about 200, or at least about 300, or at least about 400; in yet another variation, the CNT sheet substrate contains at least about 500 CNT sheets or at least about 600, or at least about 700, or at least about 800, or at least about 900, or at least about 1000 CNT sheets. In another variation, the substrate comprises between about 5 and about 1000 CNT sheets or between about 10 and about 500 CNT sheets or between about 25 and about 200 CNT sheets or between about 50 and about 100 CNT sheets. In another variation, the substrate comprises between about 5 and about 10 CNT sheets or between about 10 and about 15 CNT sheets or between about 10 and about 25 CNT sheets or between about 15 and about 20 CNT sheets or between about 20 and about 30 CNT sheets or between about 40 and about 60 CNT sheets or between about 75 and about 150 CNT sheets or between about 90 and about 110 CNT sheets.

As used herein, "pristine" when used in reference to a CNT sheet or CNT substrate, as in "a pristine CNT sheet or substrate" refers to a CNT sheet or substrate that has not been chemically modified, that is, the surface of the sheet/substrate has not been functionalized or derivatized, as defined herein. Generally, the CNT sheets prepared or received as disclosed herein were used as received or as prepared according to the methods disclosed herein (see "Preparation of a CNT sheet substrate" in Example 1) and are considered 'pristine.'

As used herein, "functionalized" when used in reference to a CNT sheet or a CNT substrate, as in 'a functionalized CNT sheet' or 'functionalized CNT substrate' refers to a chemical modification of the top and/or the bottom surface of a CNT sheet or CNT substrate. In one variation, the CNT sheet is functionalized to facilitate chemically affixing the metal centers to the sheet surface. Alternately, functionalization enables improved deposition of the metal centers on the CNT sheet.

As used herein, "derivatized" when used in reference to a CNT sheet or CNT substrate, as in 'a derivatized CNT sheet' or 'a derivatized CNT substrate,' refers to a CNT sheet or substrate in which metal and/or metal oxide centers are affixed or deposited on the top and/or the bottom of a CNT sheet surface. The metal and/or metal oxide centers can be in the form of, but are not limited to, nanoparticles as agglomerates, homogeneous or mostly homogeneous dispersions, or aggregates. In one variation, the derivatization refers to a CNT sheet or CNT substrate in which no more than 10% or no more than about 25% of the CNT surface area exposed to the derivatization process is covered by the metal and/or metal oxide. In another variation, no more than about 50% of the chemically available CNT surface area is covered; alternately, no more than about 75% is covered.

When a derivatized CNT sheet or CNT substrate is referred to as a catalyst, the composition has the effect of enabling a chemical reaction, such as, but not limited to, the conversion of carbon dioxide to one or more of carbon monoxide, methane, ethane, higher order hydrocarbons or any combination thereof, to proceed at a faster rate or under different conditions (e.g. at a lower temperature) than otherwise possible. As an electrocatalyst, the derivatized CNT sheet or CNT substrate responds to the application of current by initiating catalytic activity.

As used herein, 'electrode structure' typically refers to a printed circuit board ('PCB') electrically connected to a CNT sheet substrate; the CNT sheet substrate may be pristine, functionalized, derivatized, or otherwise treated as disclosed herein. One example of an electrode structure is shown by the cartoon in FIG. 1D, comprising a copper pattern attached to electrical wires and a PCB, containing the necessary electrical connections.

In one aspect, the present application discloses a method of preparing 'thin' fabricated CNT sheet substrates comprising between about 5 and about 100 CNT sheets from 'thick' CNT sheet substrates comprising at least about 200 CNT sheets. Thin fabricated CNT sheet substrates were prepared according to the methods disclosed herein; the resulting substrate was electrochemically stable and had enhanced capacitive performance compared to a CNT sheet substrate comprising 200 CNT sheets. As shown herein, the experimental data displayed correlation between decreasing number of CNT sheets in the substrate and larger specific capacitances. Energy and power density correspondingly increased as the number of CNT sheets in the substrate decreased.

In another aspect, the present application discloses a CNT sheet or CNT substrate derivatized with one or more metal centers. In one embodiment, the one or more metal centers comprises one or more of Cu, Pt, Ru, Fe, Zn, Ti, Pd, Mn, Mg, Sn, Ni, Rh, Al, Ag, Au, CuO, $Cu_2O$, $TiO_2$, $MnO_2$, MgO, $Al_2O_3$, $Fe_2O_3$, PdO, SnO, NiO, AgO, AuO, Ag/Ti, Pt/Ru, Ag/$TiO_2$, Pt/$Al_2O_3$, Rh/$Al_2O_3$, and Pd/$Fe_2O_3$. In another embodiment, the one or more metal centers comprises one or more of Cu, Pt, Ru, Fe, Zn, Ti, Pd, Mg, Sn, Ni, Rh, Al, Ag, Au, CuO, $Cu_2O$, $TiO_2$, MgO, $Al_2O_3$, $Fe_2O_3$, PdO, SnO, NiO, AgO, AuO, Ag/Ti, Pt/Ru, Ag/$TiO_2$, Pt/$Al_2O_3$, Rh/$Al_2O_3$, and Pd/$Fe_2O_3$. In yet another embodiment, the one or more metal centers comprises one or more of Cu, Pt, Ru, Fe, Zn, Ti, Pd, Mn, Mg, Sn, Ni, Rh, Al, Ag, Au, Ag/Ti and Pt/Ru. In another embodiment, the one or more metal centers comprises one or more of Cu, Pt, Ru, Fe, Zn, Ti, Pd, Mg, Sn, Ni, Rh, Al, Ag, Au, Ag/Ti and Pt/Ru. In another variation, the one or more metal centers comprises one or more of Cu, Ti, Pt, Ag, and Au or alternately comprises one or more of CuO, $Cu_2O$, $TiO_2$, MgO, $Al_2O_3$, $Fe_2O_3$, PdO, SnO, NiO, AgO, and AuO. Alternately, the one or more metal centers comprises one or more of Ag/$TiO_2$, Pt/$Al_2O_3$, Rh/$Al_2O_3$, and Pd/$Fe_2O_3$. In yet another variation, the one or more metal centers comprises Cu or Ti or alternately comprises one or more of CuO, $Cu_2O$, or $TiO_2$, or alternately comprises Ag/$TiO_2$. In a further variation, the one or more metal centers comprises Cu, CuO, $Cu_2O$, $TiO_2$, Ag/$TiO_2$, Pt, Ag, Au or combinations thereof.

In another aspect, the present application discloses a CNT sheet or CNT substrate derivatized with one or more metal centers selected from the group of Cu, Pt, Ru, Ti, Pd, Sn, Ag, Au, CuO, $Cu_2O$, $TiO_2$, PdO, SnO, AgO, AuO, Ag/Ti, Pt/Ru, Ag/$TiO_2$, Sn/$TiO_2$, Pt/$TiO_2$, Au/$TiO_2$, and Pt/$Al_2O_3$. In one embodiment, the one or more metal centers comprises one or more of Cu, Pt, Ti, Pd, Ag, Au, Ag/Ti and Pt/Ru. In another embodiment, the one or more metal centers comprises one or more of Cu, Ti, Pt, Ag, and Au. In yet another embodiment, the one or more metal centers comprises one or more of CuO, $Cu_2O$, $TiO_2$, PdO, SnO, AgO, and AuO. Alternately, the one or more metal centers comprises one or more of Ag/$TiO_2$, Sn/$TiO_2$, Pt/$TiO_2$, Au/$TiO_2$, and Pt/$Al_2O_3$.

In one aspect, the present application discloses a catalyst comprising any metal-derivatized CNT sheet or a metal-derivatized CNT substrate as described above. In one variation, the catalyst is an electrocatalyst; in another variation, the catalyst is a photoelectrocatalyst.

In one embodiment, the metal-derivatized CNT substrates disclosed herein are used in the conversion of carbon dioxide to one or more of carbon monoxide, methane, ethane, higher order hydrocarbons or any combination thereof. In another embodiment, the catalyst of the present application is used in an energy storage device, in a fuel cell electrode, in the filtration of biological contaminants from a biological sample, in the filtration of volatile organic compounds from a sample, or as a biosensor.

In one aspect, the present application discloses a method of converting carbon dioxide to one or more carbon monoxide, methane, ethane, higher order hydrocarbons or a combination thereof comprising exposing carbon dioxide to a catalyst as described above or exposing carbon dioxide to a metal-derivatized CNT sheet or metal-derivatized CNT sheet substrate as described above. Alternately, the present application discloses each of a method of filtering biological contaminants from a biological sample and a method of filtering volatile organic compounds from a non-biological sample comprising passing the biological sample or non-biological sample comprising biological or VOC contaminants respectively through or past a metal-derivatized CNT sheet or a metal-derivatized CNT substrate as disclosed herein and separating the unwanted contaminants from the sample. In yet another aspect, the present application discloses each of an energy storage device, a fuel cell electrode, and a biosensor each of which comprise a metal-derivatized CNT sheet or a metal-derivatized CNT substrate as disclosed herein.

In another aspect, the present application discloses a method of preparing a CNT sheet or CNT substrate derivatized with one or more transition metal centers comprising: (a) treating a CNT sheet or CNT substrate with oxygen plasma yielding a functionalized CNT sheet or functionalized CNT substrate; and (b) depositing one or more transition metals on the functionalized CNT sheet or functionalized CNT substrate. In one variation, the depositing comprises sol-gel deposition, electrodeposition, physical vapor deposition or chemical vapor deposition; in another variation, the depositing is only sol-gel deposition, electrodeposition, physical vapor deposition or chemical vapor deposition. In one embodiment, the electrodeposition comprises pulsed electrodeposition. In one variation the disclosed method further comprises activating the functionalized CNT sheet or functionalized CNT substrate. In one embodiment, the activation is electrochemical activation, wherein the activation optionally uses cyclic voltammetry.

In another aspect, the present application discloses a method of preparing a CNT sheet or CNT substrate derivatized with one or more transition metal centers comprising: (a) treating a CNT sheet or CNT substrate with oxygen plasma yielding a functionalized CNT sheet or functionalized CNT substrate; and (b) depositing one or more transition metals on the functionalized CNT sheet or functionalized CNT substrate via electrodeposition, wherein the method does not comprise electrochemically activating the functionalized CNT sheet or functionalized CNT substrate.

Using a CNT sheet substrate with excellent electrical conductivity, thermal, and chemical stability properties yields a flexible 3D electrode. Metals which can be deposited onto CNT sheets in accordance with the methods of the present application include but are not limited to Cu, Pt, Ru, Fe, Zn, Ti, Pd, Mn, Mg, Sn, Ni, Rh, Al, Co, Ag, and Au. The metal centers can be deposited as metal-oxides, such as CuO, $Cu_2O$, $TiO_2$, $MnO_2$, MgO, $Al_2O_3$, $Fe_2O_3$, PdO, SnO, NiO, AgO, and AuO, as mixed metal systems, such as Ag/Ti or Pt/Ru, or as mixed metal-oxides, including, but not limited to, Ag/$TiO_2$, Pt/$Al_2O_3$, Rh/$Al_2O_3$, and Pd/$Fe_2O_3$. As exemplified herein, some of the metal centers can be used as electrocatalysts for the conversion of carbon dioxide to hydrocarbons. In one embodiment, the metal affixed to the CNT sheet substrate is copper; in another embodiment, the metal is $TiO_2$ or alternately is Ag/$TiO_2$.

When the metal deposited on the CNT sheets is $TiO_2$, the deposition pH and deposition time of the $TiO_2$ nanoparticles can be varied, thereby influencing the photoresponse of the resulting CNT-$TiO_2$ sheet substrates.

An SEM image of a CNT sheet substrate (top view) is shown in FIG. 1A and a side view of the substrate comprising about 200 sheets, having an overall thickness of about 10 μm, is shown in FIG. 1B. FIG. 1C is an SEM image of a Cu-derivatized CNT sheet substrate containing metal centers affixed to both sides of the substrate.

As disclosed herein, a CNT sheet substrate has been treated to enable efficient deposition of metal and metal oxides on the CNT surface. When the deposited metal is copper, it acts as a highly effective catalytic reaction site for the electrochemical reduction of $CO_2$ to $CH_4$ (as well as CO and $C_2H_4$) without requiring any binder or an additional metal layer. A cartoon of an electrode as disclosed herein is shown in FIG. 1D, along with examples of a working electrode before and after pulsed electrochemical deposition of a metal on the functionalized CNT sheet substrate affixed to the electrode structure. In another example, the deposited metal is $TiO_2$ and the resulting electrode can be used as a photoelectric catalyst.

The metal derivatized CNT sheet substrates, prepared according the methods disclosed herein, have a variety of different applications, due to the electrocatalytic properties and structural robustness of the products. In particular, the metal-derivatized CNT sheets and metal-derivatized CNT substrates disclosed can be used in fuel cell electrodes, as composites for energy storage devices, as filters to remove contaminants, either biological or VOCs (volatile organic compounds). In addition, the products of the current application can be used as biosensors.

In another aspect, the present application discloses a method for fabricating of a CNT sheet substrate, the method comprising: (a) providing a first CNT sheet substrate having a first thickness defined by a number of CNT sheets; (b) providing a template sheet having an aperture therein, the aperture having a predetermined dimension; (c) adhering the template sheet to the first CNT sheet substrate; and (d) pulling the template sheet away from the first CNT sheet substrate to form a second CNT sheet substrate of a second thickness and having the predetermined dimension of the aperture, wherein the second thickness is not as great as the first thickness. In one embodiment, the number of CNT sheets that define the first thickness of the first CNT sheet substrate is less than about 1000 CNT sheets or less than about 500 CNT sheets or less than about 250 CNT sheets. In yet another embodiment, the number of CNT sheets that define the first thickness of the first CNT sheet substrate ranges from about 25 to about 200 sheets. In another embodiment, step (b) comprises providing two template sheets, each having an aperture therein, each aperture having a predetermined dimension therein, optionally wherein the predetermined dimension of each aperture is same. Alternately, or in addition, step (c) comprises adhering one template sheet to a first surface of the first CNT sheet substrate and adhering the other template sheet to a second surface of the first CNT sheet substrate opposite the first surface. Alternately or in addition, step (d) comprises pulling the template sheets away from the first CNT sheet substrate to form a second CNT sheet substrate of a second thickness and having the predetermined dimension of the aperture, wherein the second thickness is not as great as the first thickness. In one variation of any of the disclosed aspects or embodiment, the method comprises repeating steps (a)-(d) one or more additional times, with each repeat starting with the CNT sheet substrate formed at the completion of steps (a)-(d).

EXAMPLES

Example 1. Preparation of a Cu-Derivatized Carbon Nanotube Sheet Electrode

Preparation of a CNT Sheet Substrate

The CNT sheets used in the following examples were prepared generally according to the methods disclosed in Pöhls, J. H., Johnson, M. B., White, M. A., Malik, R., Ruff, B., Jayasinghe, C., Schulz, M. & Shanov, V. (2012). "Physical properties of carbon nanotube sheets drawn from nanotube arrays." Carbon, 50(11), 4175-4183 or as disclosed in Malik, R.; Alvarez, N.; Haase, M.; Ruff, B.; Song, Y.; Suberu, B.; Shereen, D.; Mast, D.; Gilpin, A.; Schulz, M.; Shanov, V. Recent Advances in Circuits, Communications and Signal Processing 2013, ISBN: 978-1-61804-164-7, 327-335.

Typically, the CNT sheets were produced from multi-walled carbon nanotubes (MWCNT) arrays. The sheets were drawn from 0.5 mm high CNT arrays, synthesized by a water-assisted chemical vapor deposition (CVD) process. Ethylene ($C_2H_4$) gas was used as a carbon precursor in order to obtain spinnable CNT arrays. The synthesized CNT arrays were aligned perpendicularly to the substrate, which consisted of several layers ($Si/SiO_2/Al_2O_3$/Fe alloy catalyst). The free-standing CNT sheet substrate was fabricated from the 0.5 mm length MWCNT array by pulling a bundle of nanotubes from one side of the aligned CNT array. The sheet was then attached to a Teflon® belt and drawn at a rate of ca. 17 mm/s. The rotation of the belt caused accumulation of the formed CNT ribbon on the Teflon® belt and formation of a CNT sheet substrate with controllable dimensions and thickness. The array on the platform was linearly translated by one half of its width per revolution of the belt thus allowing newly formed sheets to overlap previously laid ribbon and thereby securing lateral uniformity within the substrate. The fabricated 200 layer CNT sheets were densified layer by layer using acetone while the ribbon was located on the belt and simultaneously exposed to the tension caused by the drawing procedure, thereby maintaining the longitudinal nanotube orientation and the original dimensions obtained during densification. The 200 layer CNT sheet substrates were characterized by scanning electron microscopy (SEM). The obtained images revealed good tube alignment and a cross-section thickness of about 10 μm.

Preparation of an Electrode Structure

Referring now to FIG. 1D, a PCB (printed circuit board) pattern was designed using a flexible polymer composite. In one alternative, a silicon wafer can be used. The PCB was electrically connected using copper/carbon tape to a CNT sheet substrate comprising about 200 CNT sheets (2 cm×2 cm×10 μm (as in FIG. 1D). The sheet resistance was typically <1Ω from end to end, which is lower than that of the ITO (~15 Ω/sq) In place of copper/carbon tape, alternate electrical connections known to those of skill in the art can be used, including but not limited to silver paste/painting, conducting epoxy and/or lead soldering. To protect the electrical connections from unintended reaction, they can be coated with an insulator, such as silicone. As shown in FIG. 1D, a CNT sheet substrate, 10, was affixed to a PCB, 20, containing electrical connections, 30, which were attached to electrical wires, 40, used to complete the system.

In an alternative method of preparation, the CNT sheet substrate prepared as above is not affixed to the PCB, but is treated according to the method outlined below and is thereafter attached to the PCB.

Oxygen Plasma Treatment of CNT Substrate Electrode

The $O_2$ plasma treatment of the CNT substrate electrode was performed in a discharge chamber (M4L™ RF gas plasma system, PVA TePla America, Corona, Calif., United States of America). The 200 layered pristine CNT sheet substrate was exposed to the plasma produced from $O_2$ (50 sccm) and Ar (50 sccm) gas with a nominal power of about 35 W. The pressure was fixed at 500 mTorr. Typically, the exposure lasted for 5 minutes.

Electrochemical Activation

To activate the CNT sheet substrate that had been treated with oxygen plasma, the sheet, held by the PCB, was electrochemically cycled (10 cycles) from about −1.5 to about +1.5 V at room temperature and atmosphere in 0.1 mM $CuSO_4.5H_2O$ at pH 2.8, adjusted by 0.1 M $H_2SO_4$ with KCl.

Copper Deposition

Each CNT sheet electrode was immersed in the solution for 5 min. A standard electrochemical cell using a potentiostat (Gamry Instruments, Warminster, Pa.) was used with a counter electrode (a platinum plate of 2 cm×2 cm) and an Ag/AgCl reference electrode. All experiments were carried out at atmospheric pressure and room temperature (25±1° C.) and solutions were pre-purged with nitrogen for 15 min to reduce the concentration of oxygen. Pulsed electrodeposition (PED) of copper was performed in 0.1 mM $CuSO_4.5H_2O$ at pH 2.8, adjusted by 0.1 M $H_2SO_4$ with KCl. at −0.8 V and 5 Hz for 5 min. The Cu-derivatized CNT sheet substrates were then rinsed with DI water and ethanol.

Figure 2A:
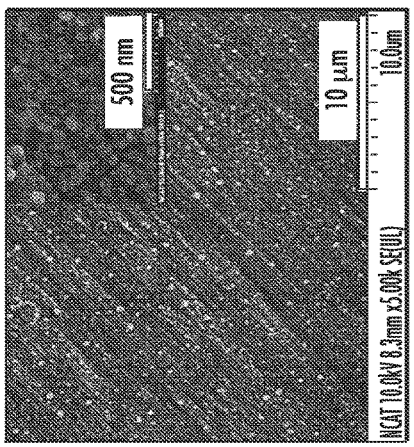
FIGS. 2A-2F show SEM images of Cu pulse-electrode-posited on a CNT sheet substrate after one of three different pretreatments.
Figure 2B:
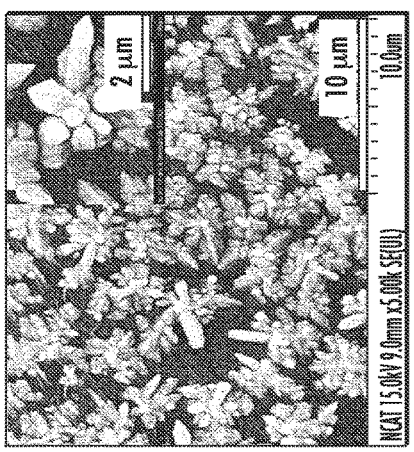
Figure 2C:
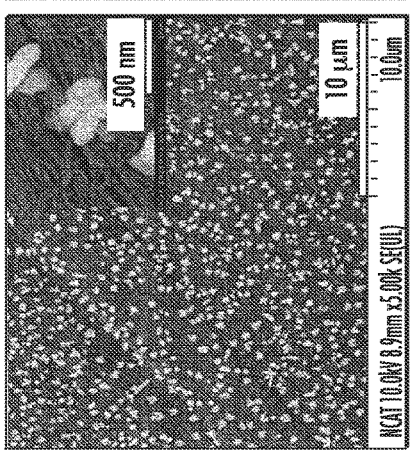
Figure 2D:
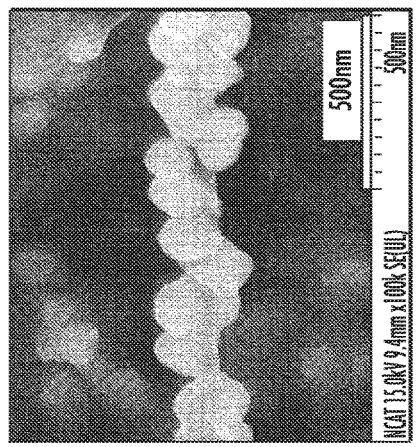
Figure 2E:
Figure 2F:
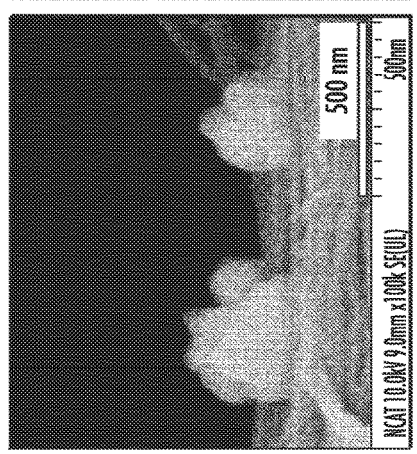
Figures 3A, 3B:
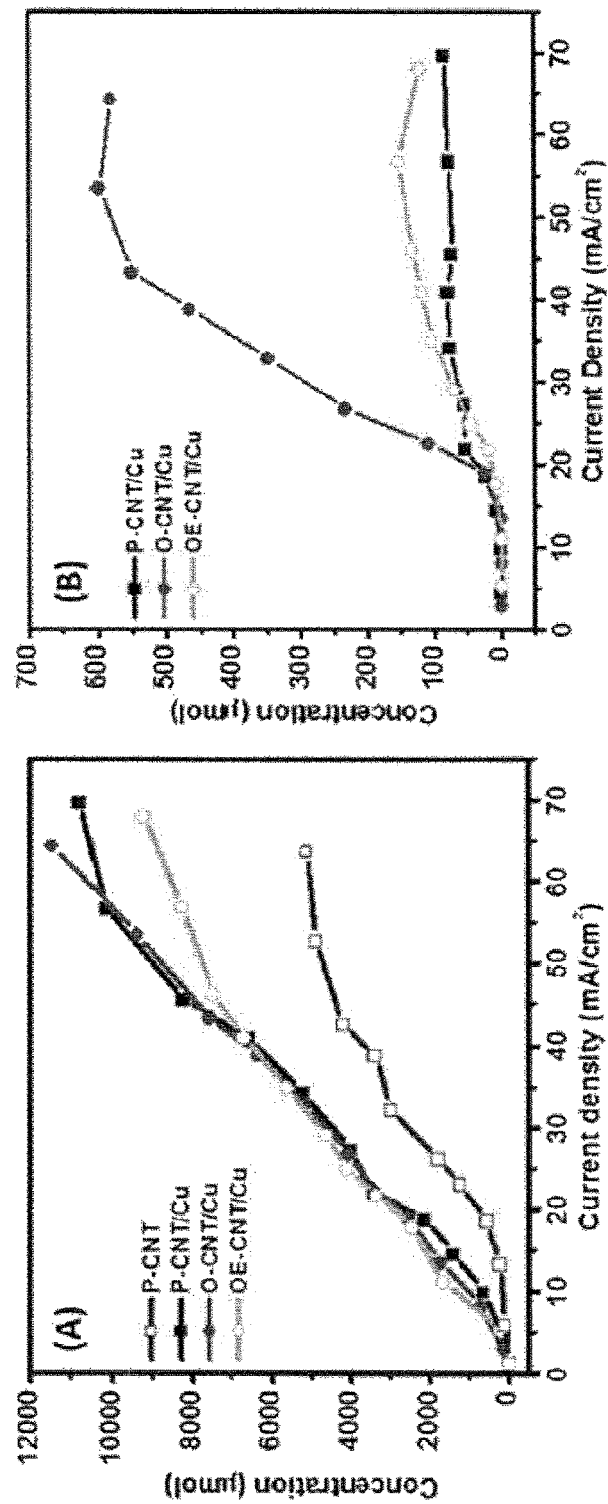
FIGS. 3A-3D are graphs showing the electrocatalytic reaction efficiency for $H_2$ evolution (FIG. 3A), $CH_4$ (FIG. 3B), CO (FIG. 3C), and $C_2H_4$ (FIG. 3D) formation using P-CNT (open squares) sheets and the three different CNT/Cu sheets (P-CNT/Cu=Cu-CNT, solid squares; O-CNT/Cu=Cu—O-CNT, solid circles; OE-CNT/Cu=Cu-OE-CNT, open circles) in 0.1 M $NaHCO_3$ at 25° C. with a $CO_2$ purge.
Figure 3D:
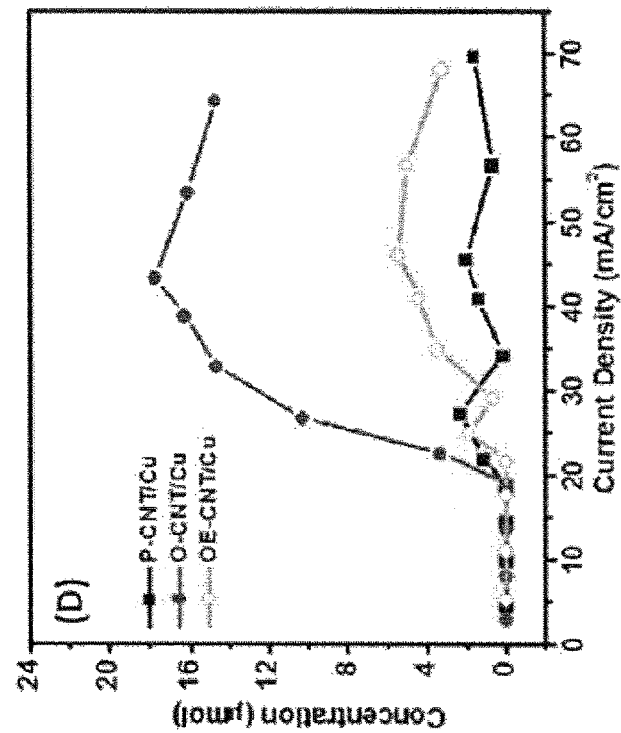
Figure 3C:
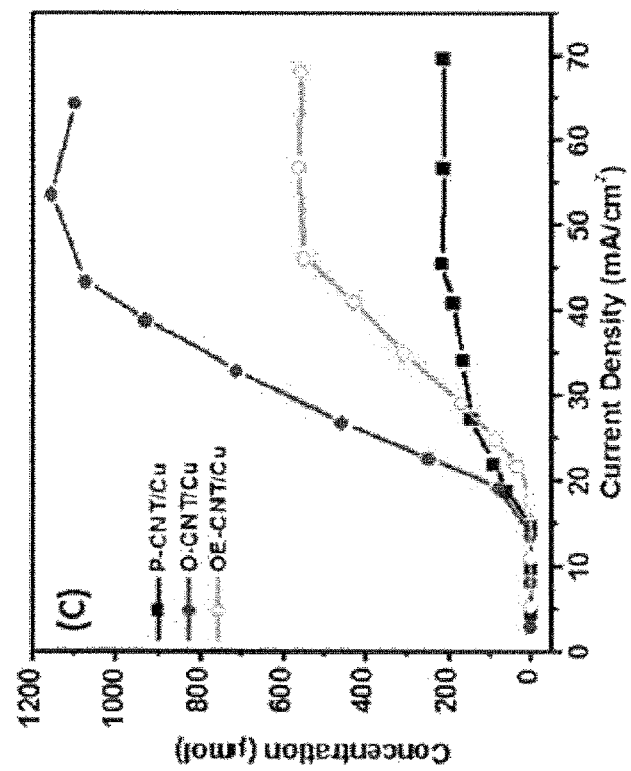
Figures 4A, 4B:
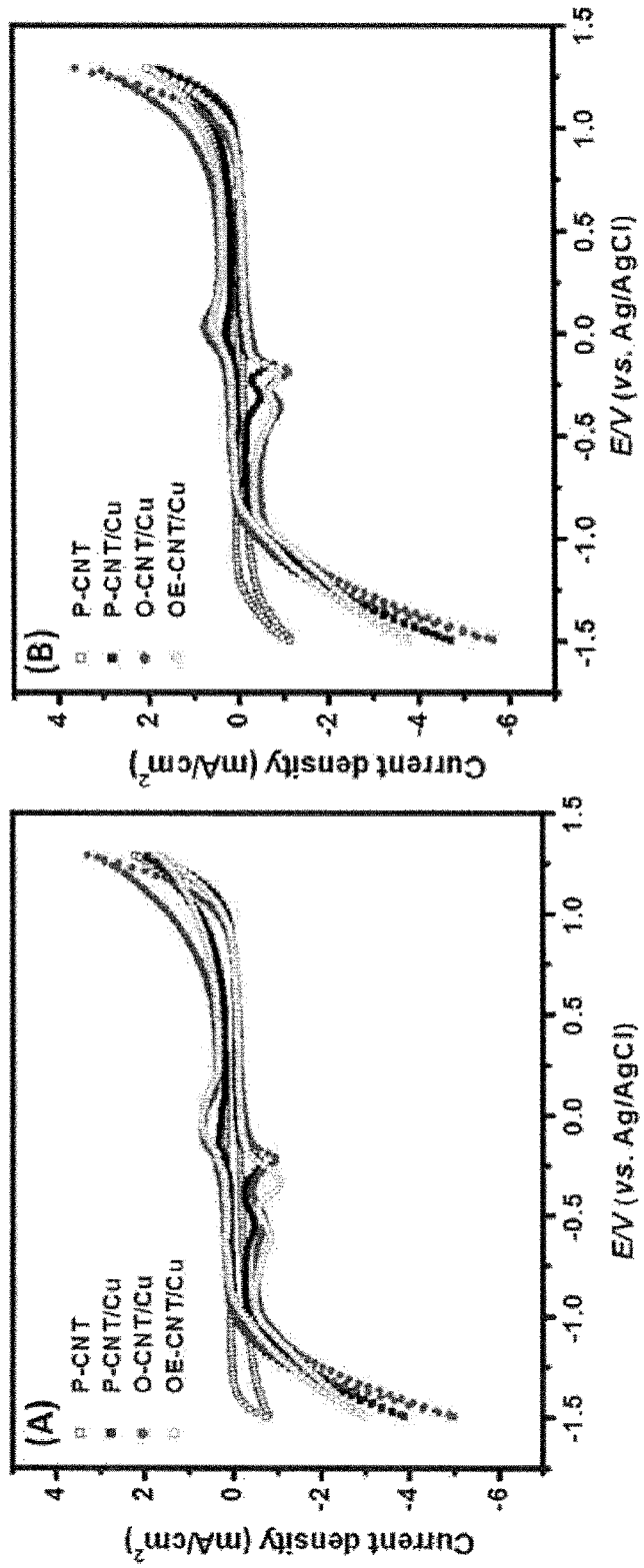
FIGS. 4A and 4B show cyclic voltammograms of a P-CNT sheet substrate (open squares) and the three different CNT/Cu sheet substrates (P-CNT/Cu=Cu-CNT, solid squares; O-CNT/Cu=Cu—O-CNT, solid circles or solid diamonds; OE-CNT/Cu=Cu-OE-CNT, open circles or open diamonds) in 0.1 M $NaHCO_3$ aqueous solution at 25° C. at a scan rate of 10 $mVs^{-1}$.

Three electrocatalysts were thus prepared:
(1) FIGS. 2A and 2D are SEM images showing a top and side view of copper electrodeposited on untreated CNT sheet substrate via PED, "P-CNT/Cu."
(2) FIGS. 2B and 2E are SEM showing a top and side view of copper pulsed electrodeposited on CNT sheet substrate treated with oxygen plasma, "O-CNT/Cu."
(3) FIGS. 2C and 2F are SEM showing a top and side view of copper deposited on CNT sheet substrate treated by electrochemical activation of the surface after treatment with oxygen plasma "OE-CNT/Cu."

Based on data from Raman spectra the defect/graphite ratios ($I_D/I_G$ ratios) of the various CNT substrates, P-CNT sheets, O-CNT sheets and OE-CNT sheets, were 0.83, 1.15, and 1.25 respectively.

The copper was deposited, coalesced and formed crystalline islands (grain formation and anisotropic growth) on P-CNT sheets and O-CNT sheets. However, the metal centers of O-CNT/Cu sheets was larger and more homogeneous. Without being bound by theory, it is believed that the presence of weakly bound oxygen atoms and oxidized defects at the CNT sheet surface created by $O_2$ plasma induced formation of Cu—O bonds and promoted nucleation for strong Cu binding The copper particles on OE-CNT/Cu sheets were observed as agglomerated spheres. Without being bound by theory, it is believed that electrochemical redox cycling following $O_2$ plasma increased the defect area of CNT sheets and chemically activated sites on the surface for metal deposition. From the population density, surface area and diameter estimation from SEM images, the metal centers of P-CNT/Cu sheets were generally spherical bundles with an average diameter of about 130 nm. The copper particles on O-CNT/Cu sheets were cylinders of different size with an average diameter and height of about 400 nm and 1 μm, respectively. The copper particles on OE-CNT/Cu sheets were hemispheres with an average diameter of about 80 nm. Noting that copper was deposited on both the top and bottom of the CNT sheets and assuming similar shapes/distributions on both surfaces, the surface areas of copper particles were calculated to be approximately 5.4 $cm^2$, 24.7 $cm^2$, and 12.2 $cm^2$ respectively. Average grain sizes were calculated using the Debye-Scherrer equation on (111), (200) reflections from X-ray diffraction (XRD) patterns, yielding an average of about 37.8 nm for the Cu deposited on CNT sheets; only signals for copper peaks were observed in the XRD. The average grain size was consistent with SEM imaging.

Electrochemical Reduction of Carbon Dioxide by Electrocatalyst.

$CO_2$ reduction of CNT substrates, P-CNT sheets and three different CNT/Cu sheets, were determined by various applied currents in $CO_2$ saturated 0.1 M $NaHCO_3$ (380 mL) aqueous solution with pH of 6.7. Electrochemical reduction experiments were conducted in a three electrode electrochemical cell. The electrolyte (0.1 M $NaHCO_3$, 380 mL) was saturated with ultra pure $CO_2$ (99.9999%, Airgas, Greensboro, N.C., United States of America) at a continuous flow rate of 10 mL/min $CO_2$ for 1 hour (298 K, pH 7.0). During the 15 minutes of $CO_2$ reduction, the electrolyte was kept under constant stirring at a current range of −1.5 to −5.0 V and voltage range of −1.0 to −70 $mA/cm^2$. At the end of the electrolysis, the gaseous products were immediately sampled and analyzed by gas chromatography. The gas chromatograph was equipped with a Hayesep-D and MS13X column and HID (Helium Ionization Detector) detector.

The CNT/Cu sheet substrates were reused without poisoning during electrocatalytic reduction of $CO_2$. The gas products from the P-CNT sheets and three different CNT/Cu sheets are summarized in FIGS. 3A-3D ((a) $H_2$, (b) CO, (c) $CH_4$, (d) $C_2H_6$). Carbon dioxide was electrocatalytically reduced to CO, $CH_4$, and $C_2H_4$ in the aqueous solution. Methane and carbon monoxide were major products and ethane a minor product in all CNT/Cu sheets. Without being bound by theory it is believed to be due to the dominant Cu (111) pattern on the surfaces, based on the XRD results. The best reduction efficiency of $CO_2$ to $CH_4$ was observed with the O-CNT/Cu sheets in the range 40-60 $mA/cm^2$. Although OE-CNT/Cu sheets have a large density of agglomerated spheres and corresponding surface coverage, the reduction efficiency of the $CO_2$ was much smaller than that of O-CNT/Cu sheets.

To promote the growth of metal particles on CNT sheets/substrates, well-defined nucleation site and spatial distribution of nucleation site were both found to be variables; these properties also were found to increase electrocatalytic reactivity. Both oxygen plasma and electrochemical modification were good methods to modify CNT sheet surfaces for nucleation sites. After activating the CNT surface using the electrochemical method and treatment with oxygen plasma, smaller sized Cu centers were deposited more uniformly and without aggregation. After treating a CNT sheet only with oxygen plasma, copper particles deposited on the surface grew directionally as a 3D crystal. The CNT sheet electrode treated with $O_2$ plasma but without subsequent electrochemical activation of the surface showed both a large catalytic surface area and large metallic contact area, and was shown to provide improved reactivity of $CO_2$ at the Cu particles, more effectively converting carbon dioxide to hydrocarbons.

Example 2. Preparation of a $TiO_2$-Derivatized CNT Sheet Electrode

A PCB pattern was designed and electrically connected to a CNT sheet substrate comprising about 200 CNT layers (2 cm×2 cm×10 μm) as described in Example 1.

In an alternative method of preparation, the CNT sheet substrate prepared as in Example 1 is not affixed to the PCB, but is treated according to the method outlined below and is thereafter attached to the PCB.

Oxygen Plasma Treatment of CNT Substrate Electrode

The $O_2$ plasma treatment of the CNT substrate was performed as described above.

$TiO_2$ Deposition with $O_2$ Plasma Treatment

In one variation, in which $O_2$ plasma treatment was used, the treated CNT sheet substrate was derivatized with $TiO_2$ using electrochemical methods.

A stable electrolytic suspension was prepared: a solution of 25 mL EtOH, 0.2 mmol $H_2O_2$, and 0.2 mmol titanium(IV) isopropoxide was added slowly with stirring to a solution of 1.2 mmol $TiO_2$ (P25) in 25 mL of $H_2O$, which was stirred vigorously for 5 minutes. The final solution was sonicated for 10 minutes; it had a pH of between 10 and 11 and maintained a homogenous medium without stirring at 298K.

All electrolytic experiments were conducted in the potentiostatic mode using a Gamry reference 600 potentiostat/galvanostat. A constant cell voltage was applied (2.0 V). After electrodeposition, CNT sheets coated with $TiO_2$ nanoparticles were rinsed with Milli-Q™ water and then dried in an open atmosphere.

The $TiO_2$-derivatized CNT sheet substrate was characterized using SEM, XRD, EDX, and XPS and Raman spectroscopies.

$TiO_2$ Deposition without $O_2$ Plasma Treatment

In one variation, in which $O_2$ plasma treatment was not used, the CNT sheet substrate was derivatized with $TiO_2$ using electrochemical methods as described above.

Figure 5A:
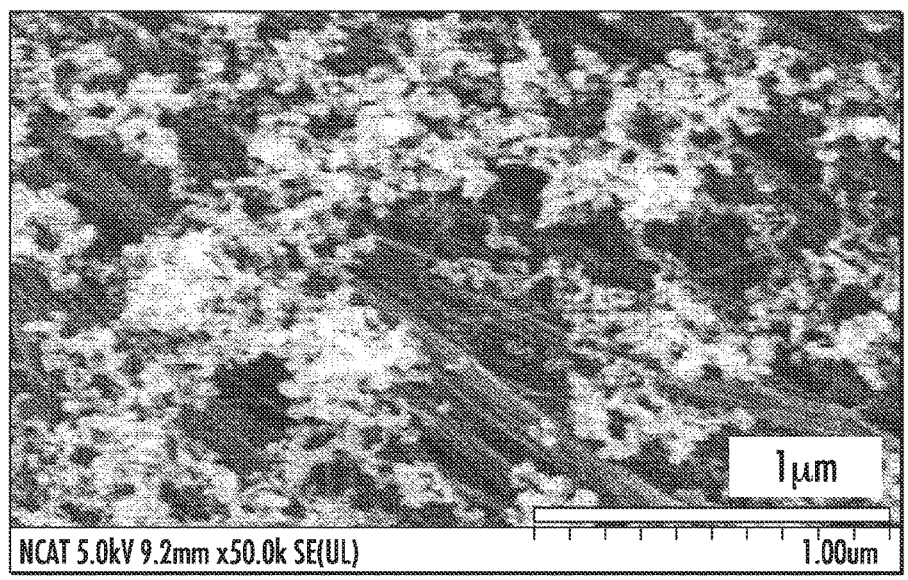
FIGS. 5A and 5B are SEM images of a $TiO_2$-CNT sheet substrate.
Figure 5B:
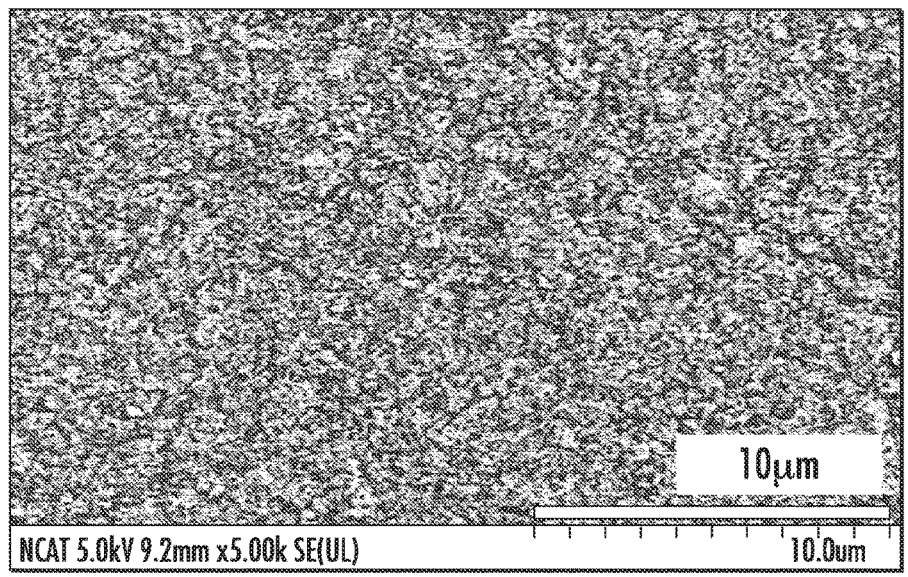

The $TiO_2$-derivatized CNT sheet substrate was characterized using SEM and EDX (FIGS. 5A and 5B). The EDX measurements for each of carbon, oxygen and titanium are identified in Table 1.

TABLE 1

EDX measurements of $TiO_2$-derivatized CNT sheet substrate

| Element | weight percent |
| --- | --- |
| Carbon | 13.13 |
| Oxygen | 57.62 |
| Titanium | 29.25 |

Generally treatment with oxygen plasma yielded stable thinner layers of $TiO_2$, while $TiO_2$ deposited without oxygen plasma treatment was found to be thicker, but less stable.

Example 3A. Preparation of an Ag/$TiO_2$-Derivatized CNT Sheet Electrode

A PCB pattern was designed and electrically connected to a CNT sheet substrate comprising about 200 CNT layers (2 cm×2 cm×10 μm) as described in Example 1.

In an alternative method of preparation, the CNT sheet substrate prepared as in Example 1 is not affixed to the PCB, but is treated according to the method outlined below and is thereafter attached to the PCB.

Ag/$TiO_2$ Nanoparticle Synthesis

Ag/$TiO_2$ nanoparticles were synthesized according to the methods previously described [Ko, et al., (2011). "Photochemical synthesis and photocatalytic activity in simulated solar light of nanosized Ag doped $TiO_2$ nanoparticle composite." *Composites Part B: Engineering*, 42(3), 579-583]. Typically, 0.3 g of P25 $TiO_2$ particles were added to 50 mL of 15 mM $AgNO_3$ aqueous solution with stirring; the solution pH (between 10 and 11) was reached via drop-wise addition of $NH_4OH$. The solution was irradiated in a dark room under black light blue UV lamp (GE, 15 W) with stirring at room temperature for 4-5 hr. The Ag loaded $TiO_2$ particles were collected via centrifugation, rinsed with distilled water, and dried overnight at 80° C. under vacuum. The Ag/$TiO_2$ nanoparticles were characterized by methods disclosed in Ko et al.

Oxygen Plasma Treatment of CNT Substrate Electrode

The $O_2$ plasma treatment of the CNT substrate was performed as described above.

Ag/$TiO_2$ Nanoparticle Deposition with $O_2$ Plasma Treatment

In one variation, in which $O_2$ plasma treatment was used, the treated CNT sheet substrate was derivatized with Ag/$TiO_2$ nanoparticles using electrochemical methods.

A stable electrolytic suspension was prepared comprising 1.2 nmol Ag/$TiO_2$ nanoparticles suspended in an equal mixture of EtOH and $H_2O$, which was stirred vigorously for 5 minutes, with optional sonication.

The electrolytic experiment was conducted in potentiostatic mode using a Gamry reference 600 potentiostat/galvanostat. A constant cell voltage was applied (2.0 V). After electrodeposition, CNT sheets coated with Ag/$TiO_2$ nanoparticles were rinsed with Milli-Q™ water and then dried in an open atmosphere. The Ag/$TiO_2$-derivatized CNT sheet substrate was characterized using SEM and XPS.

Ag/$TiO_2$ Nanoparticle Deposition without $O_2$ Plasma Treatment

In one variation, in which $O_2$ plasma treatment was not used, the CNT sheet substrate was derivatized with Ag/$TiO_2$ using electrochemical methods as described above.

Figure 6A:
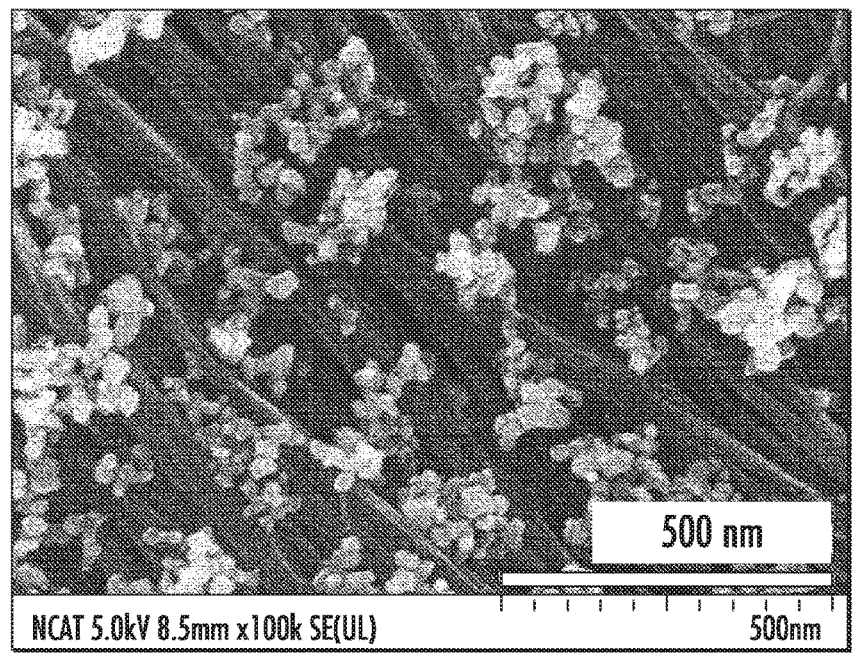
FIGS. 6A and 6B are SEM images of an $AgTiO_2$-CNT sheet substrate.
Figure 6B:
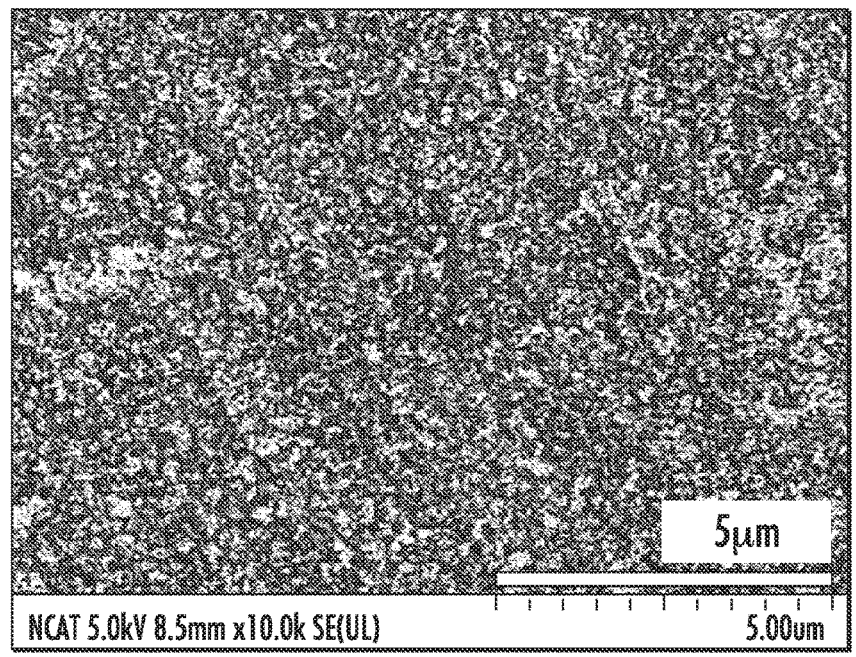

The Ag/$TiO_2$-derivatized CNT sheet substrate was characterized using SEM and EDX (FIGS. 6A and 6B). The EDX measurements for each of carbon, oxygen, silver and titanium are identified in Table 2.

TABLE 2

EDX measurements of Ag/$TiO_2$-derivatized CNT sheet substrate

| Element | weight percent |
| --- | --- |
| Carbon | 8.92 |
| Oxygen | 53.66 |
| Silver | 2.05 |
| Titanium | 34.94 |

Example 3B. Preparation of an Sn/$TiO_2$-Derivatized CNT Sheet Electrode

A PCB pattern is designed and electrically connected to a CNT sheet substrate comprising about 200 CNT layers (2 cm×2 cm×10 μm) as described in Example 1.

In an alternative method of preparation, the CNT sheet substrate prepared as in Example 1 is not affixed to the PCB, but is treated according to the method outlined below and is thereafter attached to the PCB.

Sn/$TiO_2$ nanoparticles are synthesized according to methods known in the art (see for example, Xiufeng, Zhou, et al. "Preparation of crystalline Sn-doped $TiO_2$ and its application in visible-light photocatalysis." Journal of Nanomaterials 2011 (2011): 47.)

The electrodeposition of Sn/$TiO_2$ nanoparticles on a CNT substrate is conducted as generally described above for the deposition of Ag/$TiO_2$ on a CNT substrate electrode.

The Sn/TiO$_2$-derivatized CNT sheet substrate is characterized using SEM, XRD, EDX, XPS, Raman, CV and other methods disclosed herein.

Example 3C. Preparation of Pt/TiO$_2$-Derivatized or Au/TiO$_2$-Derivatized CNT Substrate Using methods known to those of skill in the art, Pt/TiO$_2$ nanoparticles or Au/TiO$_2$ nanoparticles are prepared and deposited on a CNT substrate according to the methods disclosed herein.

The M/TiO$_2$-derivatized CNT sheet substrate is characterized using SEM, XRD, EDX, XPS, Raman, CV and other methods disclosed herein.

Example 4. Preparation of a Pt- or Au-Derivatized CNT Sheet Electrode

A PCB pattern was designed and electrically connected to a CNT sheet substrate comprising about 200 CNT layers (2 cm×2 cm×10 μm) as described in Example 1.

In an alternative method of preparation, the CNT sheet substrate prepared as in Example 1 is not affixed to the PCB, but is treated according to the method outlined below and is thereafter attached to the PCB.

Oxygen Plasma Treatment of CNT Substrate Electrode

The O$_2$ plasma treatment of the CNT substrate is optionally performed as described herein.

Metal Deposition

The optionally oxygen plasma treated CNT substrate is derivatized with Au or Pt using electrochemical methods disclosed herein, wherein the metal source solution is HAuCl$_4$ or H$_2$PtCl$_6$.x H$_2$O respectively. Alternately, the optionally treated CNT substrate is derivatized with a combination of Au and Pt, in which the source solution is comprised of both HAuCl$_4$ and H$_2$PtCl$_6$.x H$_2$O Characterization of the Metal-Derivatized CNT Sheet Substrate The M-derivatized CNT sheet substrate is characterized using SEM, XRD, EDX, XPS, Raman, CV and other methods disclosed herein.

Example 5. Fabrication of CNT Substrate and Electrochemical Deposition of a Transition Metal Oxide (TiO$_2$)

A highly-aligned CNT sheet was synthesized (see above). The CNT substrate comprising 200 CNT sheets were drawn from 0.5 mm multi-walled carbon nanotubes (MWCNT) arrays synthesized by a water-assisted chemical vapor deposition (CVD).

A electrolyte solution was prepared from two solutions, 1) solution A was prepared by mixing with 0.2 mmol H$_2$O$_2$ (CH$_3$CH$_2$OH, 99.5%, Fisher Scientific) and 0.2 mmol titanium (IV) isopropoxide (TTIP, Fisher Scientific) with absolute ethanol (CH$_3$CH$_2$OH, 99.5%, Fisher Scientific) for 15 min, 2) solution B was prepared by stirring a solution of 1.2 mmol TiO$_2$ (nanosized bicrystalline P25 50 m$^2$/g, 80% anatase, 20% rutile, Dugussa) in Milli-Q™ deionized water (Millipore) for 15 minutes. Solution B was slowly added into Solution A and 0.2 mmol ammonium hydroxide (NH$_4$OH, 30% v/v aqueous solution, Sigma Aldrich) was added to adjust pH between 10 and 11. The final solution was homogeneously dispersed at room temperature.

Electrochemical Deposition of TiO$_2$ on CNT Substrate

Deposition of TiO$_2$ on the CNT substrate prepared above was conducted using a potentiostat (Reference 600, Gamry Instrument, USA). The electrolyte was bubbled with purified N$_2$ (99.9%. Airgas, USA) for 1 hour with 5 mL/min flow rate. The CNT sheet substrate (2 cm×2 cm) served as a substrate of the working electrode. A platinum plate of 2 cm×2 cm and Ag/AgCl electrodes were used as a counter electrode and reference electrode respectively. The deposition of TiO$_2$ on the CNT sheet was carried out in the potential at 5.0 V. The CNT sheet substrates deposited with TiO$_2$ were rinsed with de-ionized water to reduce/eliminate the residual components of the suspension. The final CNT-TiO$_2$ sheet substrates were dried in air.

Characterization

Raman analysis (using a LabRAM ARAMIS (HORIBA Scientific, Edison, N.J. United States of America) with excitation laser beam (wavelength, 633 nm)) revealed the structure of the CNT sheet substrate. The surface morphology as well as the thicknesses of the prepared CNT-TiO$_2$ sheet substrates were characterized by field-emission scanning electron microscopy (FE-SEM, Hitachi 8000, 10 kV). The atomic component analysis data were obtained with energy dispersive X-ray spectroscopy (EDS) with Bruker AXS (XFlash detector 5030). Structural changes of the CNT-TiO$_2$ sheet substrates were characterized using an X-ray diffractometer (XRD, Bruker, Discover D8) with Cu K$_\alpha$ radiation (40 kV, 40 mA).

Figure 7A:
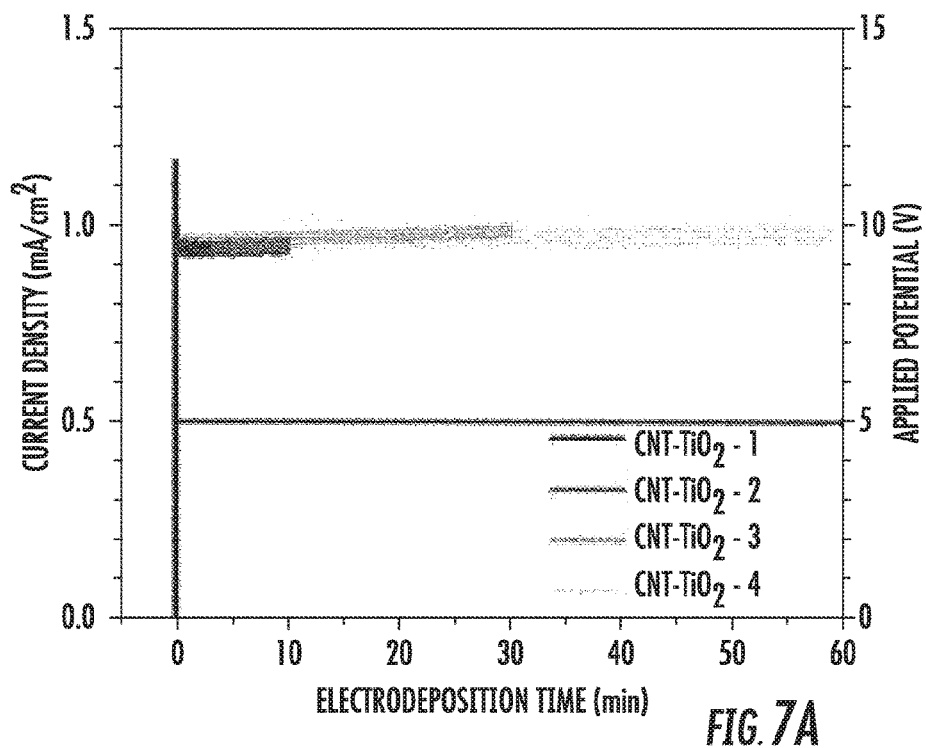
FIGS. 7A-7C summarize the electrochemical deposition conditions (applied voltage=5 V) and characterization of four different CNT-$TiO_2$ sheet electrodes.
Figure 7B:
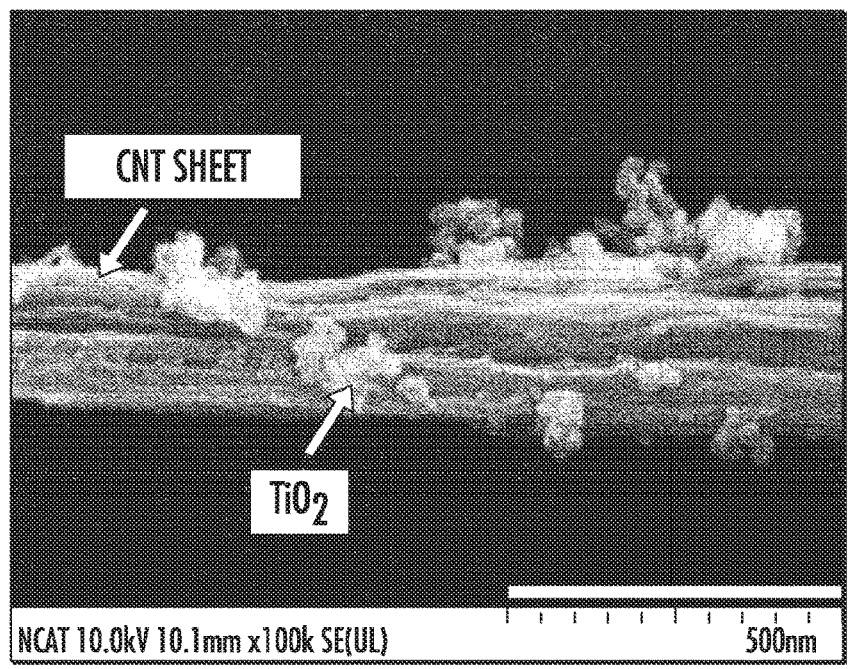
Figure 7C:
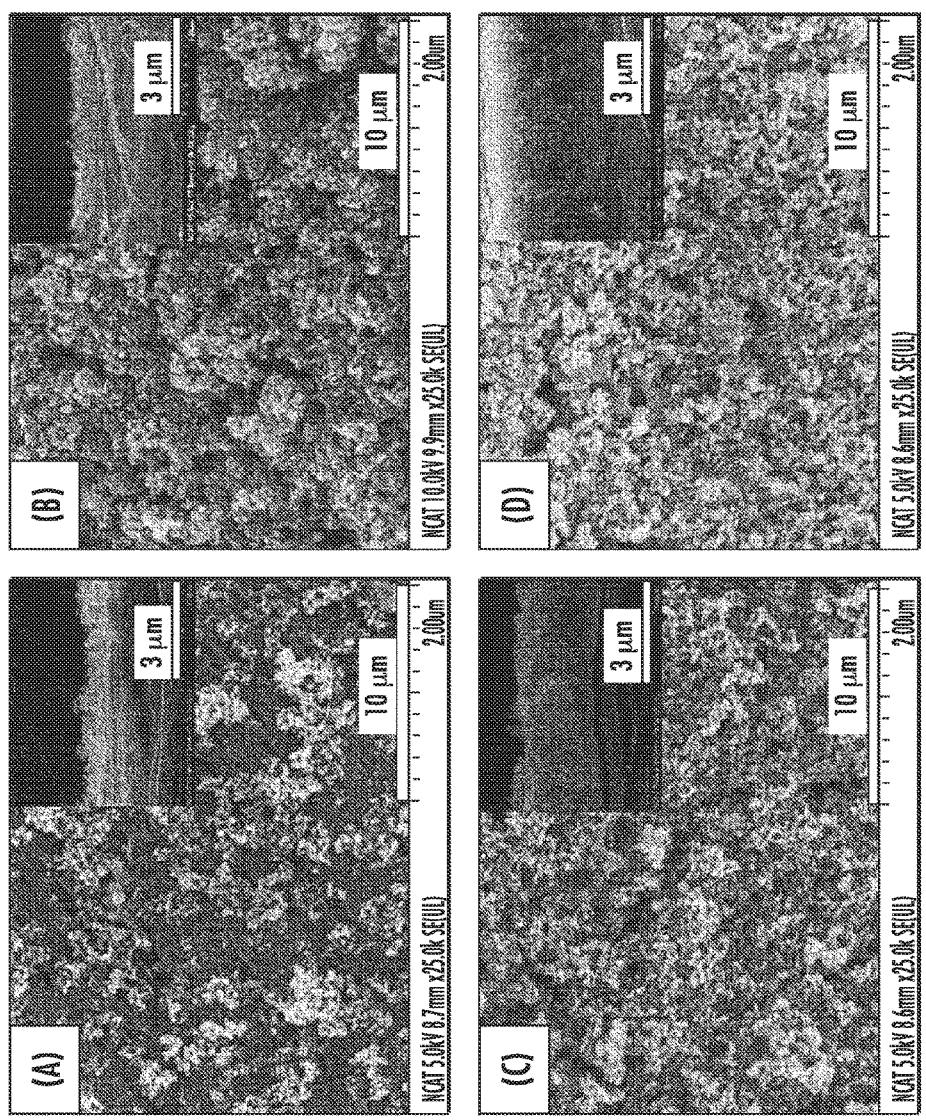

FIGS. 7A-7C show the current density of a CNT sheet electrode at applied voltage, 5.0 V, during different electrodeposition times of TiO$_2$: CNT-TiO$_2$-1 (deposition time t=3 min), CNT-TiO$_2$-2 (deposition time t=10 min), CNT-TiO$_2$-3 (deposition time t=30 min), and CNT-TiO$_2$-4 (deposition time t=60 min). As shown, the current density was substantially stable at about 1.0 mA/cm$^2$. The working electrode of the CNT sheet was activated by a cyclic voltammetric scan (potential range of ±2.5 V) for three cycles prior to electrodeposition. FIG. 7A (insert) shows the CNT sheet substrate and electrodeposited CNT-TiO$_2$-2 (t=10 min), and CNT-TiO$_2$-3 (t=30 min). As shown in FIG. 7B, TiO$_2$ (P25) nanoparticles of size 20-30 nm were deposited on both exposed surfaces of CNT sheets substrate.

The morphology of top view and cross view with the four different CNT-TiO$_2$ sheets is shown in FIG. 7C. For the CNT-TiO$_2$-1 (t=3 min) sheet, TiO$_2$ were sparsely deposited. When the electrodeposition time was increased from 10 min to 60 min, the TiO$_2$ nanoparticles were uniformly distributed with the thickness of 500 nm, 2 μm, to 3 μm respectively (insets of FIG. 7C). XRD spectra showed that TiO$_2$ nanoparticles were uniformly deposited on the CNT sheet. EDS elemental analysis showed that the relative amount of deposited TiO$_2$ increased with increasing electrodeposition time.

Example 6 Application: Electrochemical and Photoactive Study of CNT-TiO$_2$ Sheet Substrates In cyclic voltammetry testing, CNT-TiO$_2$ sheet substrates were used as a working electrode, using an electrolyte of 2.5 mM K$_3$[Fe(CN)$_6$] in 0.1 M KCl solution in a three-electrode cell with an Ag/AgCl reference electrode and a platinum plate counter electrode. Prior to evaluating photoelectrochemical activity, the electrolyte was purged with N$_2$ for 1 hour at a 5 mL/min flow rate.

Figures 8A, 8B:
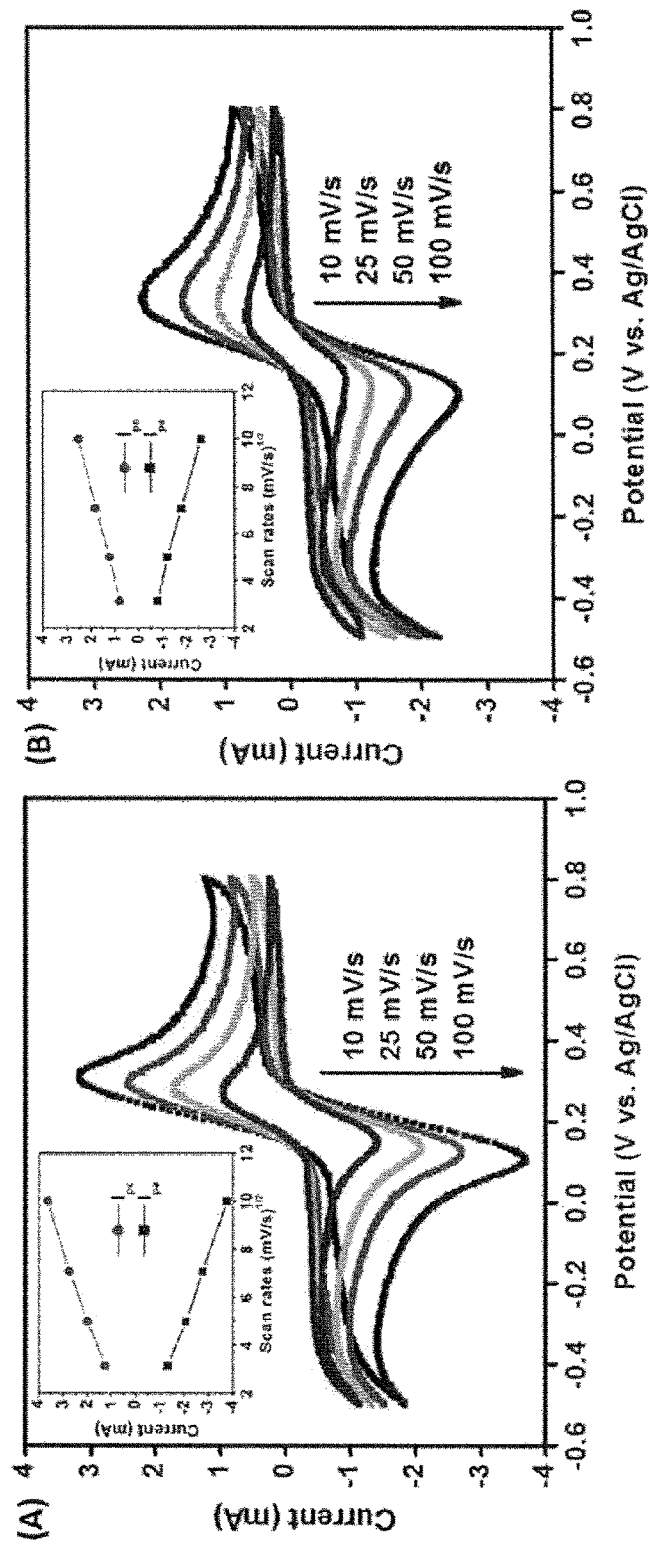
FIGS. 8A and 8B are cyclic voltammograms of electrodes recorded at scan rates of 10-100 mV/s in the presence of a 2.5 mM $K_3[Fe(CN)_6]$ as a redox probe in 0.1M KCl aqueous solution. Plot of peak currents against scan rate and plot of peak currents vs. square root of scan rate (insert; Ipc, closed circles; Ipa, closed squares) of FIG. 8A, CNT sheet substrate, and FIG. 8B, CNT-$TiO_2$-4 sheet substrates.

Cyclic voltammetry (CV) was used to characterize electrochemical properties of the CNT and the CNT-TiO$_2$-4 sheets. FIG. 8A (CNT) and FIG. 8B (CNT-TiO$_2$-4) show the CV responses of the two different electrodes for the reduction of 2.5 mM K$_3$[Fe(CN)$_6$] in 0.1 M KCl at different scan rates. The peak currents and the CV peak separation ($\Delta E_p$) of Fe(CN)$_6^{3-/4-}$ increased with scan rates (see Table 3). The ratio of the reverse-to-forward peak currents, $I_{pa}/I_{pc}$ was almost unity for a redox couple. The diffusion coefficient for $[Fe(CN)_6]^{3-}$ was calculated according to the Randles-Sevcik equation:

$$i_p = 0.4463 nFAC \left(\frac{nFvD}{RT}\right)^{1/2}$$

where A represents the area of the electrode (cm$^2$), n is the number of electrons participating in the reaction, D is the diffusion coefficient of the molecule, C is the concentration of the probe molecule, and v is the scan rate (Vs$^{-1}$), F is Faraday's constant, R is the universal gas constant and T is temperature (K). The peak current was plotted against the square root of the scan rate and the slope of the linear fit ($a=i_p/v^{1/2}$) was used to determine the diffusion coefficient. The surface area of CNT-TiO$_2$ sheets electrodes was calculated (8.0004 cm$^2$) based on electrode geometry and thickness. The calculated diffusion coefficient for $[Fe(CN)_6]^{3-}$ at the CNT substrates was $4.27 \times 10^{-6}$ cm$^2$ s$^{-1}$ at the CNT sheet and $2.56 \times 10^{-6}$ cm$^2$ s$^{-1}$ at the CNT-TiO$_2$-4 sheet respectively.

TABLE 3

Electrochemical data for CNT and CNT-TiO$_2$-4 (t = 60 min) sheet electrodes by cyclic voltammetry at different sweeping rates (FIG. 8).

| Sheets | V (mVs$^{-1}$) | E$_{ps}$ (mV) | I$_{pa}$ (mA) | I$_{pc}$ (mA) | I$_{pa}$/I$_{pc}$ |
|---|---|---|---|---|---|
| CNT | 10 | 120 | 1.32 | 1.26 | 1.05 |
|  | 25 | 150 | 2.08 | 1.99 | 1.05 |
|  | 50 | 176 | 2.78 | 2.76 | 1.01 |
|  | 100 | 209 | 3.75 | 3.61 | 1.04 |
| CNT-TiO$_2$-4 | 10 | 143 | 0.79 | 0.79 | 1.00 |
| (t = 60 min) | 25 | 187 | 1.20 | 1.22 | 0.98 |
|  | 50 | 210 | 1.79 | 1.81 | 0.99 |
|  | 100 | 223 | 2.62 | 2.52 | 1.04 |

Photoactivity of the CNT-TiO$_2$ sheets was measured using the electrochemical cell in combination with pulsed ultraviolet exposure. The 100 W, 365 nm ultraviolet (UV) lamp (UVP Inc.) was used as light source (2.68 mW/cm$^2$). The illumination light intensity was measured by a UVX radiometer (UVP Inc. UVX-36 sensor). Electron impedance spectra and photocurrent densities were measured both in the dark and under illumination. The electrolyte was purged with CO$_2$ for 1 hour at a 5 mL/min flow rate before testing.

Figures 9A, 9B:
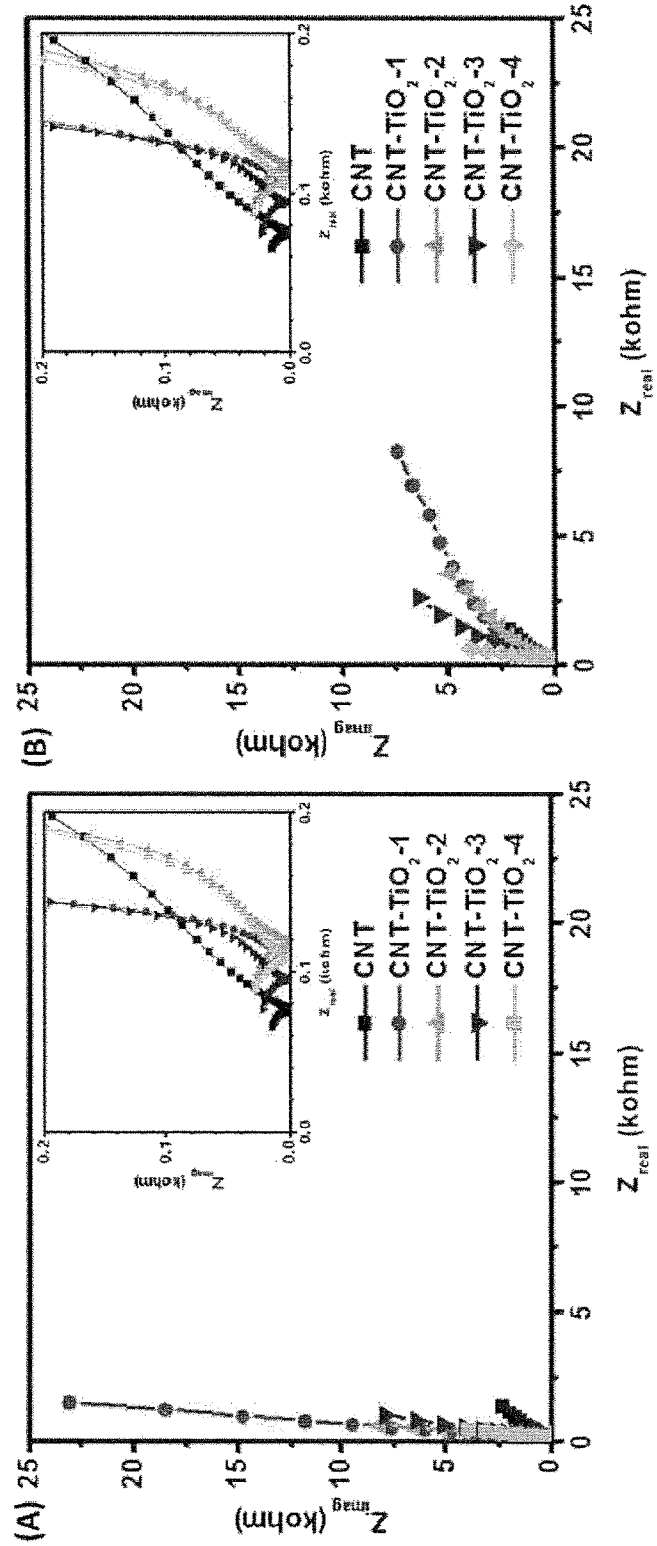
FIGS. 9A and 9B show the EIS for frequency response performances under a UV light switched on/off.

Nyquist plots for the CNT sheet substrate and the four different CNT-TiO$_2$ sheet electrodes with UV on/off exposure are shown in FIGS. 9A and 9B. At high frequency (close to 1.0 MHz), the corresponding value of the real impedance (X axis) represents the intrinsic ohmic resistance of the internal resistance or equivalent series resistance (ESR) of the electrode material and electrolyte. As shown in FIGS. 9A and 9B (insets), regardless of the UV exposure, the real part of impedance had similar value: 0.04 kΩ for all electrodes.

A lower interfacial charge transfer resistance was observed for the CNT sheet substrate than for the four different CNT-TiO$_2$ sheet substrates, indicating an interfacial nature of the deposited TiO$_2$ nanoparticles on the CNT substrate. As shown in FIG. 9B, the thicker the TiO$_2$ deposited on the CNT sheets, the smaller the impedance and capacitance at low frequency range under UV irradiation conditions, whereas the properties of the CNT sheet electrode were not affected by UV irradiation. This suggests that thin layers of TiO$_2$ nanoparticles on a CNT sheet helped achieve highly efficient carrier transport and separation efficiency from the TiO$_2$ nanoparticles to the CNT sheets substrate.

FIG. 10A shows the current-voltage curves (linear sweep voltammetry) of the CNT sheet substrate and CNT-TiO$_2$-2 sheet substrates performed from −0.4 to 0.8 V versus SCE at a scanning rate of 10 mVs$^{-1}$. Under UV irradiation, a significant increase in photocurrent density was observed on the CNT-TiO$_2$-2 sheets, whereas that of the CNT sheet were not affected by irradiation. This suggests that the TiO$_2$ nanoparticles are well deposited on CNT sheet substrate and electrons of the photo-generated electron-hole pairs were transferred to aligned CNT sheet electrode. As shown in FIG. 10B, the transient photocurrent of the all working electrodes was measured with a constant bias voltage of 0.2 V (vs SCE) under ultraviolet light irradiation ($\lambda$=365 nm, 2.68 mW/cm$^2$) with 30 sec light on/off cycles. The transient photocurrent responses of the electrodes, the CNT sheet and the four different CNT-TiO$_2$ sheets, were recorded via several on-off cycles of irradiation. A pronounced rise in the photocurrent responses was observed for all CNT-TiO$_2$ sheets under UV light illumination. This photocurrent is generally attributed to the generation and separation of photogenerated electron-hole pairs at the CNT-TiO$_2$-electrolyte interface under irradiation. The 500 nm thickness CNT-TiO$_2$-2 sheets showed the highest photocurrent intensity. The four different CNT-TiO$_2$ sheet substrates exhibited significantly higher photocurrent than that of the CNT sheet substrate, while the CNT sheet substrate exhibited weak photocurrent under UV illumination. Without being bound by theory, this was thought to be caused by the electron-hole pair generation in the CNT due to the favorable energetics of their electronic band structures.

The photocurrent responses on CNT sheet substrate and CNT-TiO$_2$-3 sheet substrates in the 0.1M KCl were recorded (see FIGS. 11A and 11B in two environments: 1) N$_2$ saturated electrolyte under UV light on/off and 2) CO$_2$ saturated electrolyte under UV light on/off). When using N$_2$ and CO$_2$ saturated electrolyte, the CNT sheets generated very small photocurrent, presumably because an electron-hole pair is not generated regardless of the illumination. The CNT-TiO$_2$ sheet electrodes however, behaved differently in the two saturated electrolytes. Using CO$_2$ saturated electrolyte, the photocurrent was 3 times higher than that of N$_2$ saturated electrolyte under irradiation. Without being bound by theory, it is thought that CO$_2$ helped electron-hole separation and collection on CNT-TiO$_2$ electrode.

As demonstrated herein, CNT-TiO$_2$ can be used as a photoactive catalyst of as a component part in a photoactive catalyst. In particular, CNT-TiO$_2$ has applications including, but not limited to solar energy conversion and storage, fuel cells, and environment remediation.

Example 7. Applications of Metal/Metal Oxide Derivatized CNT Substrates

The CNT sheet substrates derivatized with metal and/or metal oxides disclosed herein can be used in the conversion of carbon dioxide to one or more of carbon monoxide, methane, ethane, higher order hydrocarbons or any combination thereof. in the filtration of biological contaminants from a biological sample, or in the filtration of volatile organic compounds from a sample. Alternately, the derivatized CNT sheet substrates disclosed herein can used in an energy storage device, in a fuel cell electrode, or as a biosensor.

Example 8. Preparation of a 'Thin' CNT Sheet Substrate

Preparation of 200 CNT Sheet Substrate

A CNT sheet substrate comprising about 200 CNT layers (2 cm×2 cm×10 µm) was prepared according to the method described in Example 1 ("Preparation of a CNT sheet substrate"). Typically, the CNT sheet substrate used in the following was cut to about 30 mm×5 mm.

Fabrication of a CNT Sheet Substrate Comprising Fewer than 200 CNT Sheets

Referring now to FIGS. 12A-12C, an electrode pattern was drawn using Silhouette Studio software and two template sheets (each being Silhouette double side adhesive sheets, AS1 and AS2, were cut using CAMEO print (Silhouette, United States of America), using the geometry: A) inner size of 10 mm width×20 mm length and B) outer size of 20 mm width×30 mm length (FIGS. 12A-12C, which show adhesive sheet, AS1 and AS2, each having an aperture, H therein, to provide a window, W, of a predetermined dimension). While the predetermined dimension includes length and width herein in the context of a rectangular example, the predetermined dimension can comprise any shape and dimension thereof. For example, the predetermined dimension can comprise a diameter of a circle.

As-prepared 200 CNT sheet substrate, SH, was cut to 20 mm width×30 mm length. Two template sheets (each being self-adhesive) AS1 and AS2, were adhered to the CNT sheet substrate, SH— one to the top and one to the bottom (see FIGS. 12A and 12B) to form a system, S. The three layered system, S, was kept under a 5 pound weight for at least about 5 minutes. Each template sheet, AS1 and AS2, was then pulled away from one another at a 30-degree angle, which separated the 200 CNT sheet substrate into two substrates, SH' and SH", each comprising about 100 CNT sheets and each attached to one template sheet, AS1 or AS2.

The repeating of steps is referred to generally in FIG. 12C through the mathematical statement (½")($L_i$), where $L_i$ is the initial number of CNT sheet layers and n is the number of repeats.

Additional template sheets were cut as above and in FIGS. 12A-12C, in the manner of a window. Each template sheet was adhered to the side of a 100 CNT sheet substrate which was not already affixed to an template sheet, kept under a 5 pound weight for at least about 5 minutes and then the two opposing template sheets on a single substrate comprising 100 CNT sheets were pulled away from one another at a 30 degree angle to yield two 50 CNT sheet substrate, each attached to one template sheet. This process was repeated to reduce the substrates in a stepwise manner: from about 200 CNT sheets to about 100 CNT sheets; from about 100 CNT sheets to about 50 CNT sheets; from about 50 CNT sheets to about 25 CNT sheets; and from about 25 CNT sheets to about 12.5 CNT sheets, based on equal mathematical division of CNT sheets to each template sheet. Generally, the resulting substrates of differing numbers of CNT sheets were 20 mm long by 0.5 mm wide and the thickness was determined by the number of CNT sheets.

After reaching a substrate comprising approximately 12.5 CNT sheets, the substrate was transparent as well as free-standing, meaning that the substrate had three dimensional structural robustness and no additional binder was necessary to hold the CNT sheets together. A free-standing substrate did not require either binder, glass or silicon support to maintain its physical integrity.

The electrochemical properties of each substrate comprising varying number of CNT sheets were explored. Using the free-standing substrates prepared according to the methods disclosed herein, the electrochemical measurements did not require any added binder or conductive physical support.

Physical Characterization

Raman analysis was performed on pristine 200 CNT sheet substrates using a LabRAM ARAMIS (HORIBA Scientific) with excitation laser beam wavelength of 633 nm. The surface morphology was characterized by field-emission scanning electron microscope (FE-SEM, Hitachi 8000, 10 kV).

Raman analysis showed three characteristic peaks corresponding to the D, G, and G' bands observed at 1328 cm$^{-1}$, 1580 cm$^{-1}$, and 2641 cm$^{-1}$ (FIG. 13). Without being bound by theory, the D band of the disordered carbon mainly corresponds to sp$^3$ hybrid bonding and the G band of the graphitized carbon contains sp$^2$ hybrid bonding. The ratio of $I_D/I_G$ was 0.77 for the 200 CNT sheet substrate. The G' band of the second-order harmonic of the D mode is typically caused by two-phonon scattering.

Electrochemical Measurements

The electrochemical measurements were done in a three-electrode setup: a CNT sheet substrate was the working electrode, a platinum wire electrode and an Ag/AgCl electrode served as counter and reference electrodes respectively. The cyclic voltammetry (CV), constant current charge-discharge, and electrochemical impedance spectroscopy (EIS) were measured using Reference 600TM potentiostat (Gamry Instrument, United States of America) in 6 M KOH aqueous electrolyte at room temperature.

The specific capacitances of the electrodes, $C_{spe}$ were calculated according to:

$$C_{spe} = \frac{i \times \Delta t}{\Delta V \times m} \qquad (1)$$

where I (in Ampere) is the constant discharge current, Δt (in seconds) is the time for a full discharge, m (in grams) indicates the weight of the active materials in the electrode, and ΔV (in Volts) represents the potential drop during discharge.

The energy density (E) and power density (P) were calculated from the charge/discharge data according to:

$$E = \frac{1}{2}CV^2 \qquad (2)$$

$$P = \frac{E}{\Delta t} \qquad (3)$$

where C is the calculated specific capacitance, V is the voltage window (0.6 V minus the IR drop), and Δt is the discharge time.

The columbic efficiency, η, was estimated as:

$$\eta = \frac{\Delta t_d}{\Delta t_c} \times 100\% \qquad (4)$$

where $\Delta t_d$ and $\Delta t_c$ represent the discharge and charge time, respectively.

As measured, the resistance of the 200 CNT sheet substrate as affixed to the PCB as disclosed herein (2 cm×2 cm) is less than 1Ω, which includes both the bulk resistance of the substrate and the contact resistance to the PCB.

As shown in FIGS. 14A-14D, CVs were performed to study the effect of varying the number of layers in the CNT sheet electrodes on the electrochemical behavior of those electrodes. FIGS. 14A and 14B show the CVs of representative CNT sheet electrodes: about 200 layers and about 12.5 layers. The CVs were rectangular-shaped within the applied potential.

shows a more remarkable slope and no distinct semi-circle was observed in high frequency region. It is well known that the semi-circle is related to the presence of an interface between the electrode and the current collector and the electrical charge transfer in the electrode material due to the Faradic process. All of the substrates comprising CNT sheets were used directly as the electrode and the current collector simultaneously. This suggests that CNT sheets fabricated from thick CNT sheets according to the methods disclosed herein can directly be a binding free electrode without a separate current collector.

TABLE 4

Electrochemical parameters of equivalent circuits obtained from best fit to impedance data for the CNT sheet substrates (FIG. 15B).

| Layers | $R_s$ (Ω) | $CPE_L$ (S · s$^n$) | $n_1$ | $R_L$ (Ω) | $CPE_{DL}$ (S · s$^n$) | $n_2$ | $R_{CT}$ (Ω) | $Z_W$ (S · s$^{1/2}$) |
|---|---|---|---|---|---|---|---|---|
| 12 | 11.16 | $1.58 \times 10^{-4}$ | $6.77 \times 10^{-1}$ | 11.55 | $4.41 \times 10^{-5}$ | $9.69 \times 10^{-1}$ | $2.56 \times 10^5$ | $-2.30 \times 10^9$ |
| 25 | 3.543 | $1.10 \times 10^{-3}$ | $7.24 \times 10^{-1}$ | 2.67 | $9.53 \times 10^{-4}$ | $9.01 \times 10^{-1}$ | $1.83 \times 10^4$ | $-4.60 \times 10^5$ |
| 50 | 1.924 | $7.49 \times 10^{-4}$ | $8.07 \times 10^{-1}$ | 1.242 | $1.53 \times 10^{-3}$ | $9.11 \times 10^{-1}$ | $1.45 \times 10^5$ | $-32.61$ |
| 100 | 2.731 | $2.36 \times 10^{-3}$ | $6.83 \times 10^{-1}$ | 2.317 | $2.31 \times 10^{-3}$ | $8.90 \times 10^{-1}$ | $5.75 \times 10^4$ | $-1.431$ |
| 200 | 1.85 | $1.38 \times 10^{-2}$ | $7.11 \times 10^{-1}$ | 1.57 | $7.04 \times 10^{-3}$ | $9.76 \times 10^{-1}$ | $2.66 \times 10^3$ | $-3.15$ |

The peak current response of the electrode comprising about 200 CNT sheets is roughly 80 times larger than that of the substrate comprising about 12.5 CNT sheets. FIG. 14C shows CVs of different number of CNT sheets in CNT substrates at constant scan rate, 1000 mV/s. With an increase in the number of CNT sheets, an increase in current density was observed. The substrates showed typical capacitance behavior (rectangular shape). FIG. 14D shows the current response of substrates comprising different number of CNT sheets at scan rates from 25 mV/s to 3000 mV/s. As the scan rate and number of layers increased, the current linearly increased at constant potential, 0.2 V.

Electrochemical impedance measurements were carried out to understand the electrochemical performance of the CNT sheet substrates as a supercapacitor. FIGS. 15A and 15B shows the impedance spectra of the CNT substrates comprising different numbers of CNT sheets as Nyquist plots and the Bode plots; the dots represent experimental data, and lines represent a model of an equivalent circuit. The equivalent circuit shown in FIG. 15C can be used to explain the impedance plots: $R_s$ is the electrolyte resistance (the equivalent series resistance, ESR), $CPE_L$ and $R_L$ are the capacitance and resistance of CNT sheet electrode, and $CPE_{DL}$ and $R_{CT}$ are the double-layer capacitance and charge-transfer resistance, respectively. $Z_W$ is the Warburg impedance related to the ionic diffusion into the CNT sheet. The fitted data for all circuit parameters are shown in Table 4.

In FIG. 15A, all substrates comprising CNT sheets behave like supercapacitors at low frequency. As shown in the inset of FIG. 15A, the substrate comprising about 12.5 CNT sheets also has a supercapacitor property. In high-to-mid frequency range, the CNT sheet substrates are thinner, shapes with a slope of about 45° are clearer. These CNT sheets exhibit a "Warburg like" shape for double layer charging of porous electrode. In case of thinner substrates (comprising fewer CNT sheets), the electrolyte can likely permeate into the voids of the individual CNT sheets. In the case of the substrate comprising about 12.5 CNT sheets, it FIG. 16A-16C show the capacitive performance of the four substrates comprising different number of CNT sheets. FIG. 16A shows the comparison of a typical charge/discharge curves of CNT sheet electrodes between 0 V and 0.6 V at constant current of 1.5 mA. The charge curves of the CNT sheet substrates having between about 100 and about 25 CNT sheets were nearly symmetric with fast charging and discharging capabilities compared to their corresponding discharge curves in the potential range. These electrodes demonstrated a high reversibility between charge and discharge processes at cycle performance. On the other hand, substrates comprising about 200 CNT sheets showed an asymmetric behavior during the charge/discharge process. Since it is difficult for electrolyte to penetrate quickly into the dense CNT sheet substrates, charge achieving time for the substrate comprising 200 CNT sheets is slow in comparison. FIGS. 16B and 16C demonstrate the specific capacitance, coulombic efficiency, energy density and power density of the four different substrates, respectively. Specific capacitances of the four substrates increased with decreasing number of CNT sheets in the substrate. In particular, the specific capacitance of the substrate comprising 25 CNT sheets increased more than others. The coulombic efficiency of the substrate comprising 50 CNT sheets reached almost 100%, implying good charge/discharge reversibility for the supercapacitor (FIG. 16B). Energy and power densities of the four substrates showed an inverse relationship with the number of CNT sheets. This behavior could be ascribed to the depletion of the immobilization of the charge carriers during charge and discharge processes. Generally, substrates comprising between about 25 and about 50 CNT sheets had an adequate stack and large surface area and exhibited better electrochemical properties than substrates comprising at least about 200 CNT sheets as shown by the higher specific capacitance, higher coulombic efficiency, higher energy density, and higher power density in FIG. 16.

TABLE 5

Capacitance performance summary of substrates comprising different numbers of of CNT sheets fabricated according to the methods disclosed herein (at constant current 1.5 mA).

| Parameters | About 12.5 Sheets* | About 25 Sheets | About 50 Sheets | About 100 Sheets | About 200 Sheets |
|---|---|---|---|---|---|
| Charge time (s) | 4 | 5 | 3 | 14 | 50 |
| Discharge time (s) | 3 | 4 | 3 | 4 | 6 |
| Energy density (Wh/kg) | 0.50 | 2.57 | 1.09 | 0.78 | 0.54 |
| Power density (W/kg) | 606 | 2312 | 1312 | 702 | 325 |
| Charge/discharge efficiency (%) | 75 | 80 | 100 | 29 | 12 |

*Result for substrate comprising approximately 12.5 CNT sheets was measured at constant current 0.15 mA.

A comparison of the results of the different substrates prepared according to the methods disclosed herein are summarized in Table 5. Substrates comprising between about 25 and about 50 CNT sheets have better supercapacitor performance than the other substrates measured at constant current of 1.5 mA. Specific capacitance of the substrate comprising approximately 12.5 CNT sheets, 10.10 F g$^{-1}$ was also measured at relatively low current such as 0.15 mA. The electrochemical properties of the substrate comprising about 12.5 CNT sheets decreased, as shown in Table 5. Poor interfacial contact of the about 12.5 CNT sheets in the substrate might be one reason for the high internal resistance of the supercapacitor due to increasing resistance due to the loose connections between layers (FIG. 15). That is, capacitance efficiency of the dense and thick CNT sheet substrates are not fully decreased, the reason may be that the surface area for accessing part of CNT sheets strands of electrolyte is smaller than that of thinner CNT substrates. Electrochemical stability testing demonstrated that the CNT sheet substrates were stable for multiple charging and discharging the cells (minimum of 1000 cycles).

Example 9. Preparation of a 'Thin' Cu-Derivatized CNT Sheet Substrate

A 'thin' CNT sheet substrate comprising between about 12.5 and about 100 CNT sheets is prepared according to the methods of Example 8.

The thin CNT sheet substrate is derivatized with copper metal centers according to the methods of Example 1.

The Cu-derivatized thin CNT sheet substrate is characterized using standard electrochemical methods disclosed herein, including cyclic voltammetry and EIS charge/discharge response, as well as SEM, XRD, EDX, and Raman spectroscopy.

Example 10. Preparation of a TiO$_2$-Derivatized CNT Sheet Electrode

A 'thin' CNT sheet substrate comprising between about 12.5 and about 100 CNT sheets is prepared according to the methods of Example 8.

The thin CNT sheet substrate is derivatized with TiO$_2$ according to the methods of Example 2 or Example 5.

The TiO$_2$-derivatized thin CNT sheet substrate is characterized using standard electrochemical methods disclosed herein, including cyclic voltammetry and EIS charge/discharge response, as well as SEM, XRD, EDX, and Raman spectroscopy.

Example 11. Preparation of an M/TiO$_2$-Derivatized CNT Sheet Electrode

A 'thin' CNT sheet substrate comprising between about 12.5 and about 100 CNT sheets is prepared according to the methods of Example 8.

The thin CNT sheet substrate is derivatized with Ag/TiO$_2$, Sn/TiO$_2$, Pt/TiO$_2$, or Au/TiO$_2$, according to the methods of Example 3.

The M/TiO$_2$-derivatized thin CNT sheet substrate is characterized using standard electrochemical methods disclosed herein, including cyclic voltammetry and EIS charge/discharge response, as well as SEM, XRD, EDX, and Raman spectroscopy.

Example 12. Preparation of a Pt- or Au-Derivatized CNT Sheet Electrode

A 'thin' CNT sheet substrate comprising between about 12.5 and about 100 CNT sheets is prepared according to the methods of Example 8.

The thin CNT sheet substrate is derivatized with Pt or Au according to the methods of Example 4.

The Pt- or Au-derivatized thin CNT sheet substrate is characterized using standard electrochemical methods disclosed herein, including cyclic voltammetry and EIS charge/discharge response, as well as SEM, XRD, EDX, and Raman spectroscopy.

Example 13. Uses of 'Thin' Derivatized CNT Sheet Substrates

The 'thin' CNT sheet substrates derivatized with metal and/or metal oxides disclosed herein can be used in the conversion of carbon dioxide to one or more of carbon monoxide, methane, ethane, higher order hydrocarbons or any combination thereof. in the filtration of biological contaminants from a biological sample, or in the filtration of volatile organic compounds from a sample. Alternately, derivatized CNT sheets substrates disclosed herein can used in an energy storage device, in a fuel cell electrode, or as a biosensor.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed:

1. A carbon nanotube (CNT) sheet or CNT sheet substrate derivatized with one or more metal center selected from the group of Cu, Pt, Ru, Ti, Pd, Sn, Ag, Au, CuO, Cu$_2$O, TiO$_2$, PdO, SnO, AgO, AuO, Ag/Ti, Pt/Ru, Ag/TiO$_2$, Sn/TiO$_2$, Pt/TiO$_2$, Au/TiO$_2$, and Pt/Al$_2$O$_3$, wherein said CNT sheet comprises an array of CNT aligned after synthesis of the CNT and wherein said CNT sheet substrate comprises at least two CNT sheet layers.

2. The CNT sheet or CNT sheet substrate of claim 1, wherein said one or more metal center comprises one or more of Cu, Pt, Ti, Pd, Ag, Au, Ag/Ti and Pt/Ru.

3. The CNT sheet or CNT sheet substrate of claim 2, wherein said one or more metal center comprises one or more of Cu, Ti, Pt, Ag, and Au.

4. The CNT sheet or CNT sheet substrate of claim 3, wherein said one or more metal center comprises Cu.

5. The CNT sheet or CNT sheet substrate of claim 1, wherein said one or more metal center comprises one or more of CuO, $Cu_2O$, $TiO_2$, PdO, SnO, AgO, and AuO.

6. The CNT sheet or CNT sheet substrate of claim 5, wherein said one or more metal center comprises $TiO_2$.

7. The CNT sheet or CNT sheet substrate of claim 1, wherein said one or more metal center comprises one or more of Ag/$TiO_2$, Sn/$TiO_2$, Pt/$TiO_2$, Au/$TiO_2$, and Pt/$Al_2O_3$.

8. The CNT sheet or CNT sheet substrate of claim 7, wherein said one or more metal center comprises Ag/$TiO_2$.

9. A catalyst comprising the CNT sheet or CNT sheet substrate of claim 1.

10. The catalyst of claim 9, wherein said catalyst is an electrocatalyst.

11. The catalyst of claim 9, wherein said catalyst is a photoelectrocatalyst.

12. A method of converting carbon dioxide to one or more of carbon monoxide, methane, ethane, higher order hydrocarbons or a combination thereof comprising exposing said carbon dioxide to a catalyst comprising the CNT sheet or CNT sheet substrate of claim 1.

13. The CNT sheet or CNT sheet substrate of claim 1, wherein said CNT sheet substrate comprises multiple layers of free-standing CNT sheets.

14. A method of preparing a CNT sheet or CNT sheet substrate derivatized with one or more transition metal centers, wherein said CNT sheet comprises an array of CNT aligned after synthesis of the CNT and wherein said CNT sheet substrate comprises at least two CNT sheet layers, the method comprising:
(a) treating a CNT sheet or CNT sheet substrate with oxygen plasma yielding a functionalized CNT sheet or functionalized CNT sheet substrate; and
(b) depositing one or more transition metals on the functionalized CNT sheet or functionalized CNT sheet substrate.

15. The method of claim 14, wherein said depositing comprises sol-gel deposition, electrodeposition, physical vapor deposition or chemical vapor deposition.

16. The method of claim 15, wherein said electrodeposition comprises pulsed electrodeposition.

17. The method of claim 15, further comprising activating the functionalized CNT sheet or functionalized CNT sheet substrate.

18. The method of claim 17, wherein said activation is electrochemical activation.

19. The method of claim 15, wherein said method does not comprise electrochemically activating the functionalized CNT sheet or functionalized CNT sheet substrate.

20. A method for fabricating of a CNT sheet substrate, the method comprising:
(a) providing a first CNT sheet substrate having a first thickness defined by a number of CNT sheets;
(b) providing a template sheet having an aperture therein, the aperture having a predetermined dimension;
(c) adhering the template sheet to the first CNT sheet substrate; and
(d) pulling the template sheet away from the first CNT sheet substrate to form a second CNT sheet substrate of a second thickness and having the predetermined dimension of the aperture, wherein the second thickness is not as great as the first thickness.

21. The method of claim 20, wherein the number of CNT sheets that define the first thickness of the first CNT sheet substrate ranges from about 25 to about 200 sheets.

22. The method of claim 20, wherein
step (b) comprises providing two template sheets, each having an aperture therein, each aperture having a predetermined dimension therein, optionally wherein the predetermined dimension of each aperture is same;
step (c) comprises adhering one template sheet to a first surface of the first CNT sheet substrate and adhering the other template sheet to a second surface of the first CNT sheet substrate opposite the first surface; and
step (d) comprises pulling the template sheets away from the first CNT sheet substrate to form a second CNT sheet substrate of a second thickness and having the predetermined dimension of the aperture, wherein the second thickness is not as great as the first thickness.

23. The method of claim 20, comprising repeating steps (a)-(d) one or more additional times, with each repeat starting with the CNT sheet substrate formed at the completion of steps (a)-(d).

* * * * *